(12) United States Patent
Sinclair et al.

(10) Patent No.: US 10,968,174 B2
(45) Date of Patent: Apr. 6, 2021

(54) SYNTHESIS OF A THIOSULFONIC ACID BY A STEP OF PERIODATE MEDIATED OXIDATIVE COUPLING OF A THIOSULFONIC ACID WITH AN ANILINE

(71) Applicant: WisTa Laboratories Ltd., Singapore (SG)

(72) Inventors: James Peter Sinclair, Old Aberdeen (GB); Sarah Louise Nicoll, Old Aberdeen (GB); John Mervyn David Storey, Old Aberdeen (GB); Christopher Paul Larch, Old Aberdeen (GB)

(73) Assignee: WisTa Laboratories Ltd., Singapore (SG)

( * ) Notice: Subject to any disclaimer, the term of this patent is extended or adjusted under 35 U.S.C. 154(b) by 0 days.

(21) Appl. No.: 16/471,674

(22) PCT Filed: Dec. 21, 2017

(86) PCT No.: PCT/EP2017/084111
§ 371 (c)(1),
(2) Date: Jun. 20, 2019

(87) PCT Pub. No.: WO2018/115292
PCT Pub. Date: Jun. 28, 2018

(65) Prior Publication Data
US 2020/0115335 A1    Apr. 16, 2020

(30) Foreign Application Priority Data
Dec. 21, 2016 (GB) .................................... 1621817

(51) Int. Cl.
C07C 381/04     (2006.01)
C07D 279/20     (2006.01)

(52) U.S. Cl.
CPC .......... *C07C 381/04* (2013.01); *C07D 279/20* (2013.01)

(58) Field of Classification Search
CPC ........................... C07C 381/04; C07D 279/20
USPC ........................................................ 544/56
See application file for complete search history.

(56) References Cited

U.S. PATENT DOCUMENTS 4,212,971 A    7/1980 Konzelman et al.

FOREIGN PATENT DOCUMENTS

| CN | 1970548 A | 5/2007 |
|---|---|---|
| CN | 105 130 926 A | 12/2015 |
| DE | 1877 1866 | 12/1877 |
| EP | 0 510 668 A2 | 10/1992 |
| EP | 0 966 957 A2 | 12/1999 |
| EP | 2 322 517 A1 | 5/2011 |
| EP | 2 430 007 B2 | 2/2014 |
| WO | WO 96/30766 A1 | 10/1996 |
| WO | WO 02/055720 A2 | 7/2002 |
| WO | WO 2006/032879 A2 | 3/2006 |
| WO | WO 2007/110627 A2 | 10/2007 |
| WO | WO 2007/110630 A1 | 10/2007 |
| WO | WO 2008/007074 A2 | 1/2008 |
| WO | WO 2010/130977 A1 | 11/2010 |

(Continued)

OTHER PUBLICATIONS

PCT/EP2017/084111, Mar. 16, 2018, International Search Report and Written Opinion.

(Continued)

*Primary Examiner* — Kahsay Habte
(74) *Attorney, Agent, or Firm* — David F. Cauble

(57) ABSTRACT

The present invention pertains generally to the field of chemical synthesis, and more particularly to methods for the chemical synthesis of a thiosulfonic acid of Formula (1) by a step of periodate mediated oxidative coupling of a thiosulfonic acid of Formula (2) with an aniline of Formula (3), as described herein. The present invention also relates to such methods which incorporate one or more additional (subsequent and/or preceding) steps, for example, to prepare compounds of Formula (5) from compounds of Formula (1); to prepare compounds of Formula (6) from compounds of Formula (5); and to prepare compounds of Formula (2) from compounds of Formula (4), as described herein.

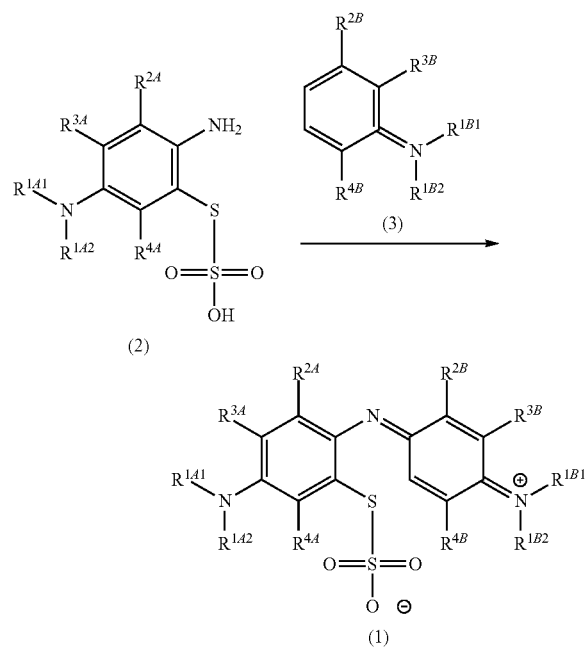

21 Claims, 4 Drawing Sheets

(56) References Cited

FOREIGN PATENT DOCUMENTS

| WO | WO 2012/107706 A1 | 8/2012 |
|---|---|---|
| WO | WO 2015/052496 A1 | 4/2015 |

OTHER PUBLICATIONS

PCT/EP2017/084111, Jul. 4, 2019, International Preliminary Report on Patentability.
GB1621817.4, Oct. 12, 2017, Search Report.
Search Report dated Oct. 12, 2017 in connection with GB1621817.4.
International Search Report and Written Opinion dated Mar. 16, 2018 in connection with Application No. PCT/EP2017/084111.
International Preliminary Report on Patentability dated Jul. 4, 2019 in connection with Application No. PCT/EP2017/084111.
Abdulrahman et al., Flow injection-Spectrophotometric determination of some catecholamine drugs. Baghdad Science Journal. Mar. 6, 2005;2(1):124-30. doi: https://doi.org/10.21123/bsj.2005.2.1.124-130.
Baltac et al., Synthesis of Dyes of Histological/Histochemical Interest. UPB Sci. Bull., Ser. B. Jan. 1, 2012;74(4)61-8.
Bernthsen, Studies in the methylene blue group. In: Justus Liebig's Annalen der Chemie. Band 230. Jul. 7, 1885. Kopp et al., Eds.:73-136. German.
Bernthsen, Studies in the methylene blue group. In: Justus Liebig's Annalen der Chemie. Band 230. Apr. 16, 1885. Kopp et al., Eds.:137-211. German.
Bernthsen, Studies in the methylene blue group. In: Justus Liebig's Annalen der Chemie. Band 251. Nov. 1, 1889. Kopp et al., Eds.:1-97. German.
Carrico et al., Oxidative coupling of peptides to a virus capsid containing unnatural amino acids. Chem Commun (Camb). Mar. 14, 2008;(10):1205-7. doi: 10.1039/b717826c. Epub Jan. 29, 2008.
Chern et al., Periodate-catalyzed oxidative coupling of aniline-derived p-aminophenol with p-xylenol as a detection method for hydroxyl radicals. Anal let. Nov. 30, 2001;34(14):2477-84.
Cohn, Information on Leuco-methylene Blue. The British Library—The World's Knowledge. May 28, 1900. Chapter 251:1567-8.
Elsohly et al., Development of oxidative coupling strategies for site-selective protein modification. Acc Chem Res. Jul. 21, 2015;48(7):1971-8. doi: 10.1021/acs.accounts.5b00139. Epub Jun. 9, 2015.
Fierz et al., Oxazine and Thiazine Dyes. In: Fudnamental Processes of Dye Chemistry. 1949. Interscience London:308-15.
Guttmann et al., On the Effect of Methylene Blue on Malaria. Berlin Clinical Weekly. Sep. 28, 1891;28(39):11 pages.
Kramer et al., Assay of Phenols and Arylamines via Oxidative Coupling. Anal. Chem. Jun. 1971;43(7):834-7.
Leventis et al., Synthesis of Substituted Phenothiazines Analogous to Methylene Blue by Electrophilic and Nucleophilic Aromatic Substitutions in Tandem. A Mechanistic Perspective. Tetrahedron. 1997;53(29):10083-92.
Lillie et al., Zinc Chloride Methylene Blude. I. Biological Stain History, Physical Characteristics and Approximation of Azure B Content of Commercial Samples. Stain Technology. 1979;54(1):33-9.
[No Author Listed] Colour Index 1971, $3^{rd}$ edition;4:4470.
Rengelshausen et al., Pharmacokinetic interaction of chloroquine and methylene blue combination against malaria. Eur J Clin Pharmacol. 2004;60:709-15. Doi: 10.1007/s00228-004-0818-0.
Schirmer et al., Methylene blue as an antimalarial agent. Redox Report. 2003;8(5):272-5. doi: 10.1179/135100003225002899.
Wang et al., Nanocrystalline $TiO_2$-catalyzed photoreversible color switching. Nano Lett. Mar. 12, 2014;14(3):1681-6. doi: 10.1021/nl500378k. Epub Feb. 20, 2014.
Wischik et al., Isolation of a fragment of tau derived from the core of the paired helical filament of Alzheimer disease. Proc. Natl. Acad. Sci. USA. Jun. 1988;85:4504-10.
Wischik et al., Modelling prion-like processing of tau protein in Alzheimer's disease for pharmaceutical development. In: Brain Microtubule Associated Proteins: Modifications in Disease. 1997. Avila et al., Eds. Amsterdam: Harwood Academic Publishers. Chapter 12:185-241.
Wischik et al., Selective inhibition of Alzheimer disease-like tau aggregation byphenothiazines. Proc. Natl. Acad. Sci. USA. Oct. 1996;93:11213-18.
Wischik et al., Structural characterization of the core of the paired helical filament of Alzheimer disease. Proc Natl Acad Sci U S A. Jul. 1988;85(13):4884-8.
Wischik et al., The molecular basis of tau protein pathology in Alzheimer's disease and related neurodegenerative dementias. In: Neurobiology of Alzheimer's Disease. 2001. Dawbarn et al., Eds. Oxford University Press. Chapter 5:103-206.

SYNTHESIS OF A THIOSULFONIC ACID BY A STEP OF PERIODATE MEDIATED OXIDATIVE COUPLING OF A THIOSULFONIC ACID WITH AN ANILINE

CROSS-REFERENCE TO RELATED APPLICATIONS

This Application is a National Stage filing under 35 U.S.C. 371 of International Patent Application Serial No. PCT/EP2017/084111, filed Dec. 21, 2017, which claims priority to Great Britain Application No. 1621817.4, filed Dec. 21, 2016. The contents of these applications are incorporated herein by reference in their entirety.

TECHNICAL FIELD

The present invention pertains generally to the field of chemical synthesis, and more particularly to methods for the chemical synthesis of a thiosulfonic acid of Formula (1) by a step of periodate mediated oxidative coupling of a thiosulfonic acid of Formula (2) with an aniline of Formula (3), as described herein. The present invention also relates to such methods which incorporate one or more additional (subsequent and/or preceding) steps, for example, to prepare compounds of Formula (5) from compounds of Formula (1); to prepare compounds of Formula (6) from compounds of Formula (5); and to prepare compounds of Formula (2) from compounds of Formula (4), as described herein.

BACKGROUND

A number of publications are cited herein in order to more fully describe and disclose the invention and the state of the art to which the invention pertains. Each of these references is incorporated herein by reference in its entirety into the present disclosure, to the same extent as if each individual reference was specifically and individually indicated to be incorporated by reference.

Throughout this specification, including the claims which follow, unless the context requires otherwise, the word "comprise," and variations such as "comprises" and "comprising," will be understood to imply the inclusion of a stated integer or step or group of integers or steps but not the exclusion of any other integer or step or group of integers or steps.

It must be noted that, as used in the specification and the appended claims, the singular forms "a," "an," and "the" include plural referents unless the context clearly dictates otherwise. Thus, for example, reference to "a pharmaceutical carrier" includes mixtures of two or more such carriers, and the like.

Ranges are often expressed herein as from "about" one particular value, and/or to "about" another particular value. When such a range is expressed, another embodiment includes from the one particular value and/or to the other particular value. Similarly, when values are expressed as approximations, by the use of the antecedent "about," it will be understood that the particular value forms another embodiment.

This disclosure includes information that may be useful in understanding the present invention. It is not an admission that any of the information provided herein is prior art or relevant to the presently claimed invention, or that any publication specifically or implicitly referenced is prior art.

Any sub-titles herein are included for convenience only, and are not to be construed as limiting the disclosure in any way.

Methylthioninium Chloride (MTC) (also known as Methylene Blue)

Methylthioninium Chloride (MTC) (also known as Methylene Blue (MB); methylthionine chloride; tetramethylthionine chloride; 3,7-bis(dimethylamino) phenothiazin-5-ium chloride; C.I. Basic Blue 9; tetramethylthionine chloride; 3,7-bis(dimethylamino) phenazathionium chloride; Swiss blue; C.I. 52015; C.I. Solvent Blue 8; aniline violet; and Urolene Blue®) is a low molecular weight (319.86), water soluble, tricyclic organic compound of the following formula:

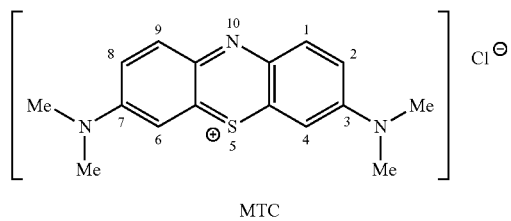

MTC

Methylthioninium Chloride (MTC) (also known as Methylene Blue), perhaps the most well-known phenothiazine dye and redox indicator, has also been used as an optical probe of biophysical systems, as an intercalator in nanoporous materials, as a redox mediator, and in photoelectrochromic imaging.

See, for example, Colour Index (Vol. 4, 3rd edition, 1971) and Lillie et al., 1979, and references cited therein.

MTC is currently used to treat methemoglobinemia (a condition that occurs when the blood cannot deliver oxygen where it is needed in the body). MTC is also used as a medical dye (for example, to stain certain parts of the body before or during surgery); a diagnostic (for example, as an indicator dye to detect certain compounds present in urine); a mild urinary antiseptic; a stimulant to mucous surfaces; a treatment and preventative for kidney stones; and in the diagnosis and treatment of melanoma.

MTC has been used to treat malaria either singly (Guttmann & Ehrlich, 1891) or in combination with chloroquine (Schirmer et al. 2003; Rengelhausen et al. 2004). Malaria in humans is caused by one of four protozoan species of the genus *Plasmodium: P. falciparum, P. vivax, P. ovale*, or *P. malariae*. All species are transmitted by the bite of an infected female Anopheles mosquito. Occasionally, transmission occurs by blood transfusion, organ transplantation, needle-sharing, or congenitally from mother to fetus. Malaria causes 300-500 million infections worldwide and approximately 1 million deaths annually. Drug resistance, however is a major concern and is greatest for *P. falciparum*, the species that accounts for almost all malaria-related deaths. Drugs or drug combinations that are currently recommended for prophylaxis of malaria include chloroquine/proguanil hydrochloride, mefloquine, doxycycline and primaquine.

MTC (under the name Virostat, from Bioenvision Inc., New York) has shown potent viricidal activity in vitro. Specifically Virostat is effective against viruses such as HIV and West Nile Virus in laboratory tests. West Nile virus (WNV) is a potentially serious illness affecting the central nervous system. The large majority of infected people will show no visible symptoms or mild flu-like symptoms such as fever and headache. About one in 150 will develop severe symptoms including tremors, convulsions, muscle weakness, vision loss, numbness, paralysis or coma. Generally, WNV is spread by the bite of an infected mosquito, but can also spread through blood transfusions, organ transplants, breastfeeding or during pregnancy from mother to child. Virostat is also currently in clinical trials for the treatment of chronic Hepatitis C. Hepatitis C is a viral infection of the liver. The virus, HCV, is a major cause of acute hepatitis and chronic liver disease, including cirrhosis and liver cancer. HCV is spread primarily by direct contact with human blood. The major causes of HCV infection worldwide are use of unscreened blood transfusions, and re-use of needles and syringes that have not been adequately sterilized. The World Health Organization has declared hepatitis C a global health problem, with approximately 3% of the world's population infected with HCV and it varies considerably by region. The prevalence in the US is estimated at 1.3% or approximately 3.5 million people. Egypt contains the highest prevalence of hepatitis C in the world, estimated at over 20% of the nation's approximately 62 million people.

MTC, when combined with light, can prevent the replication of nucleic acid (DNA or RNA). Plasma, platelets and red blood cells do not contain nuclear DNA or RNA. When MTC is introduced into the blood components, it crosses bacterial cell walls or viral membrane then moves into the interior of the nucleic acid structure. When activated with light, the compounds then bind to the nucleic acid of the viral or bacterial pathogen, preventing replication of the DNA or RNA. Because MTC is designed to inactivate pathogens, it has the potential to reduce the risk of transmission of pathogens that would remain undetected by testing.

MTC and derivatives thereof (e.g., "diaminophenothiazinium compounds") have been found to be useful in the treatment of tauopathies (such as, for example, Alzheimer's disease) (see, for example, Wischik, C. M., et al., 1996, 2002).

Oral and parenteral formulations of MTC are commercially available in the United States, usually under the name Urolene Blue®. However, these formulations contain substantial amounts of metal impurities. These impurities are highly undesirable, and many (e.g., including Al, Cr, Fe, Cu) exceed the safety limits set by European health agencies.

Consequently, there is a great need for higher purity (e.g., pharmaceutical grade purity, e.g., a purity safe for human consumption, e.g., with low or reduced metal content) diaminophenothiazinium compounds, including MTC.

MTC was first described in a German Patent in 1877 (Badische Anilin- und Soda-Fabrik, 1877). In that patent, MTC was synthesized by nitrosylation of dimethylaniline, subsequent reduction to form N,N-dimethyl-1,4-diaminobenzene, and subsequent oxidative coupling in the presence of hydrogen sulphide ($H_2S$) and iron(III) chloride ($FeCl_3$).

Iron based oxidative coupling in the synthesis of MTC was more recently discussed in CN105130926.

Bernthsen described subsequent studies of MTC and methods for its synthesis (see Bernthsen, 1885a, 1885b, 1889).

Fierz-David and Blangley, 1949, also describes methods for the synthesis of MTC from dimethylaniline, as illustrated in the following scheme:

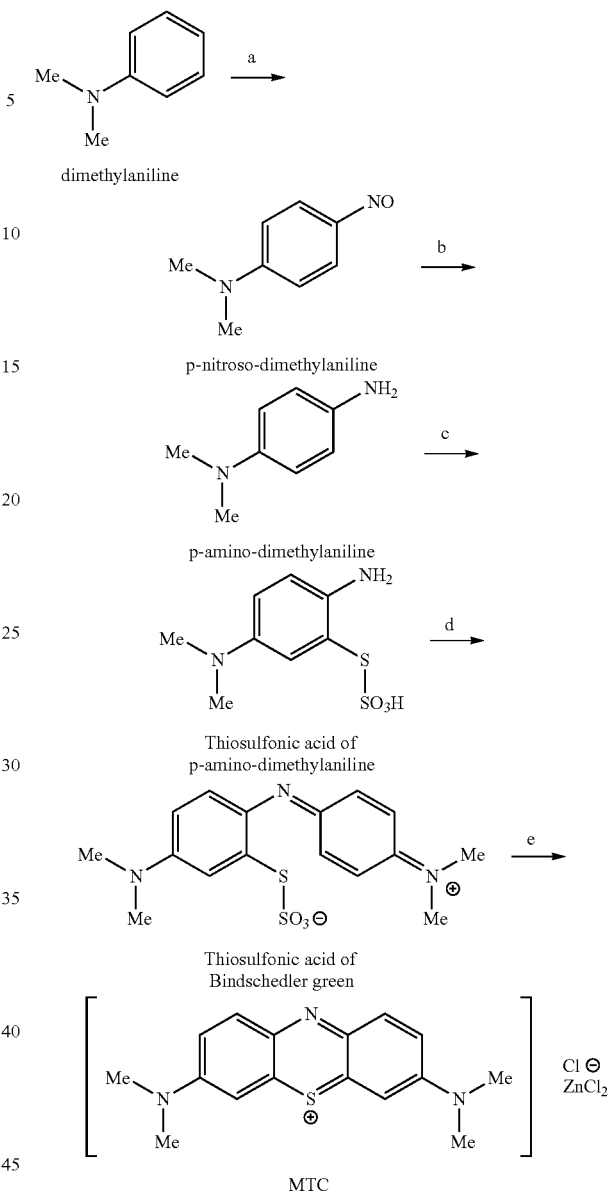

In step (a), nitrosodimethylaniline is prepared from dimethylaniline by treatment with nitrite ($NaNO_2$) in aqueous acid (HCl) solution. In step (b), the nitroso compound is reduced to form p-aminodimethylaniline using additional aqueous acid (HCl) solution using zinc dust. The metal residue after step (b) is removed by filtration and the filtrate is oxidised in the presence of thiosulfonic acid, sulphuric acid and non-reducing zinc chloride solution, step (c).

Oxidation in the presence of dimethylaniline results in the thiosulfonic acid of Bindschedlers green, step (d). This oxidation is carried out using a dichromate based oxidising agent, $Na_2Cr_2O_7$. The oxidation is then continued in the same reaction pot to provide MTC, step (e).

More specifically, a clear neutral solution of p-aminodimethylaniline is acidified ($H_2SO_4$), and a non-reducing zinc chloride solution is added ($ZnCl_2$ with $Na_2Cr_2O_7$). Aqueous aluminium sulphate ($Al_2(SO_4)_3$) and crystalline sodium thiosulphate ($Na_2S_2O_3$) are added. Aqueous sodium dichromate ($Na_2Cr_2O_7$) is added. The mixture is heated by dry steam.

Aqueous acidic (HCl) dimthylaniline is then added. Aqueous sodium dichromate ($Na_2Cr_2O_7$) is added. The mixture is heated with dry steam, and becomes dark greenish-blue in colour due to the formation of the thiosulfonic acid of Bindschedler green. An aqueous slurry of manganese dioxide or copper sulfate is added, and the mixture heated by dry steam, and the dye precipitates from the concentrated zinc chloride solution. To recover the dye from the mixture it is cooled and acidified ($H_2SO_4$) to dissolve the aluminium, manganese and chromium salts. The mixture is cooled further and the crude dye collected by filtration. Purification from water, sodium chloride and zinc chloride gives the zinc double salt of methylene blue as bronzy red crystals.

Very similar synthesis methods are described in the Colour Index (Vol. 4, 3rd edition, 1971), p. 4470.

U.S. Pat. No. 4,212,971 A and CN1970548 A describes the synthesis of MTC using manganese dioxide in the formation of the thiosulfonic acid intermediate and its subsequent oxidative coupling to the thiosulfonic acid of Bindshedler's green. The manganese dioxide is used in stoichiometric amounts in the synthesis.

Masuya et al., 1992, describe certain phenothiazine derivatives, and methods for their preparation and use in photodynamic therapy of cancer and in immunoassays utilizing chemiluminescence. The compounds are prepared by routes similar to those discussed above.

Leventis et al., 1997, describe methods for the synthesis of certain MTC analogs, which employ phenothiazine as a starting material and which add the desired 3,7-substituents by halogenation followed by amination. The authors assert that MTC is synthesized commercially by oxidation of N,N-dimethyl-p-phenylene diamine with $Na_2Cr_2O_7$ in the presence of $Na_2S_2O_3$, followed by further oxidation in the presence of N,N-dimethylamine.

Fierz-David et al., 1949, describes the synthesis of the zinc chloride double salt of MTC and the removal of zinc by chelation with sodium carbonate followed by filtration to generate zinc free methylene blue. However, the authors acknowledge that this technique cannot be used on a large scale, because the yields are poor.

WO 2006/032879 describes a method for synthesizing MTC via an oxidative coupling. The oxidative coupling is carried out according to the following scheme:

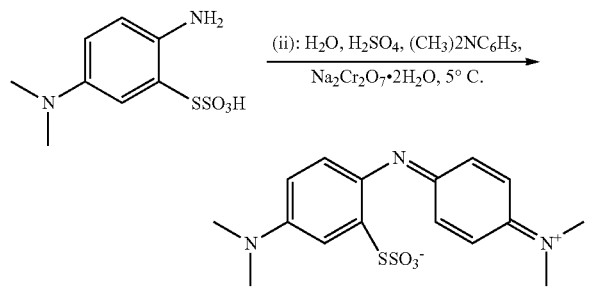

The oxidative coupling step is carried out using a dichromate oxidising agent, $Na_2Cr_2O_7$. The oxidative coupling is discussed generally on page 23 line 35 to page 25 line 28 and in the examples from page 67 to 75, therein.

EP0510668 and EP0966957 describes a method for synthesizing derivatives of MTC via an oxidative coupling. The oxidative coupling is carried out using potassium dichromate or manganese dioxide.

WO2010/130977 describes a method for synthesizing MTC via an oxidative coupling. The oxidative coupling is carried out according to the following scheme:

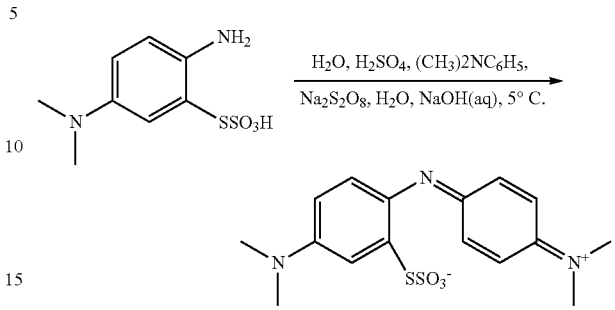

The oxidative coupling step is carried out using a persulfate oxidising agent, $Na_2S_2O_8$. A subsequent ring closure step is carried out using copper sulfate to provide MTC. This method provides MTC in 16% yield calculated over the two steps (oxidative coupling and ring closure) with 85% purity measured by HPLC peak area. The oxidative coupling is discussed generally on page 28 to page 33 and in the examples, see 'Synthesis 2', page 50 therein.

WO 2015/052496 also describes a method for synthesizing MTC via an oxidative coupling. The oxidative coupling is carried out according to the following scheme:

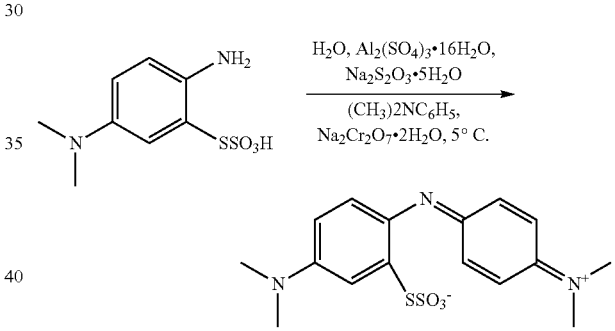

The oxidative coupling is carried out using a chromium based oxidising agent, $Na_2Cr_2O_7$. In this method, the oxidative coupling step is combined with the previous step, thiosulfonic acid formation, into a one-pot chromium mediated reaction. The oxidative coupling is discussed generally on page 21 to page 33 and in the examples therein.

Improved Methods of Synthesis

It is generally desirable that chemical compounds which are intended to be used as pharmaceuticals are provided in a form that is sufficiently free of undesired impurities. This is especially true for chemical compounds that are intended to be used as part of long-term therapy, for example, daily administration for a period of months or years (or, indeed, indefinitely).

The presence of even relatively small amounts of certain undesirable impurities can render a chemical compound unacceptable for use in therapy, for example, accordingly the specifications set by national regulatory bodies (e.g., the US Food and Drug Administration, the European Medicines Agency, etc.).

Among the many undesired impurities are certain metals, including iron (Fe), manganese (Mn) and especially chromium (Cr). For example, the European Pharmacopoeia (version 8.6) limits the amount of residual manganese that may be present in pharmaceutical MTC to less than 10 ppm. It is often extremely difficult to remove these metal impurities from a chemical compound that has been prepared by a method of chemical synthesis which used them.

For example, a method of chemical synthesis which employs, as an oxidizing agent, a chromium compound (e.g., chromate, $CrO_4^{2-}$; dichromate, $Cr_2O_7^{2-}$), a manganese compound (e.g., manganese dioxide, $MnO_2$) and/or an iron compound (e.g., iron (III) chloride, $FeCl_3$) often yields a product with residual chromium, manganese and/or iron, which cannot easily (or at all) be reduced to acceptable levels.

As discussed above, alkylthioninium salts (such as MTC) and derivatives thereof have utility in the long-term treatment of chronic conditions (such as Alzheimer's disease) and accordingly must be provided in a form with extremely low metal (including, e.g., chromium, manganese and iron) content.

Such compounds are conventionally prepared by methods of chemical synthesis which involve one or more oxidation steps which frequently use chromium, manganese and/or iron-based oxidizing agents. Consequently, the resulting product must undergo substantial purification in order to reduce the chromium and/or iron content to acceptable levels.

Accordingly, there is a need for alternative methods of chemical synthesis of such alkythioninium salts and their derivatives which avoid the need to use such metal-based (e.g., chromium-based) oxidizing agents and provide the products with high yields and purities.

The inventors have identified such methods, which are described herein. For example, alkythioninium salts of Formula (5) (such as MTC) can be prepared by methods described herein which avoid the use of chromium oxidizing agents.

More specifically, the methods described herein include the step of preparing a thiosulfonic acid of Formula (1) by a step of periodate mediated oxidative coupling of a thiosulfonic acid of Formula (2). The thiosulfonic acid of Formula (1) is then cyclized to give the corresponding thioninium compound of Formula (5).

Surprisingly and unexpectedly, the periodate mediated oxidative coupling described herein is successful and avoids the use of chromium oxidising agents. Furthermore, the periodate mediated coupling provides the desired compounds with improved yields and purity.

Consequently (and surprisingly and unexpectedly), compounds of Formula (5) can be obtained in good yield and purity without the use of chromium oxidizing agents, and thus with less need for further purification to remove residual chromium.

SUMMARY OF THE INVENTION

The present invention relates to methods for chemical synthesis which include the step of preparing a thiosulfonic acid of Formula (1) by a step of periodate mediated oxidative coupling of a thiosulfonic acid of Formula (2).

Accordingly, one aspect of the invention is a method of chemical synthesis of a compound of Formula (1):

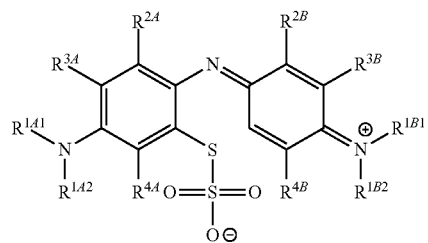

comprising a step of periodate mediated oxidative coupling, in which a compound of Formula (2):

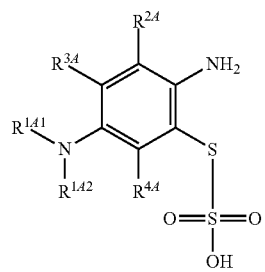

is reacted with a compound of Formula (3):

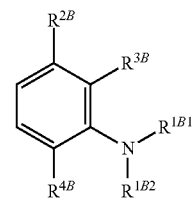

and a periodate oxidising agent;
to form said compound of Formula (1); wherein:
—$R^{1A1}$ is independently $C_{1-4}$alkyl; $C_{2-4}$alkenyl; halogenated $C_{1-4}$alkyl; $C_{5-10}$aryl; halogenated $C_{5-10}$aryl; $C_{5-10}$aryl-$C_{1-4}$alkyl; or halogenated $C_{5-10}$aryl-$C_{1-4}$alkyl;
—$R^{1A2}$ is independently $C_{1-4}$alkyl; $C_{2-4}$alkenyl; halogenated $C_{1-4}$alkyl; $C_{5-10}$aryl; halogenated $C_{5-10}$aryl; $C_{5-10}$aryl-$C_{1-4}$alkyl; or halogenated $C_{5-10}$aryl-$C_{1-4}$alkyl;
—$R^{1B1}$ is independently $C_{1-4}$alkyl; $C_{2-4}$alkenyl; halogenated $C_{1-4}$alkyl; $C_{5-10}$aryl; halogenated $C_{5-10}$aryl; $C_{5-10}$aryl-$C_{1-4}$alkyl; or halogenated $C_{5-10}$aryl-$C_{1-4}$alkyl;
—$R^{1B2}$ is independently $C_{1-4}$alkyl; $C_{2-4}$alkenyl; halogenated $C_{1-4}$alkyl; $C_{5-10}$aryl; halogenated $C_{5-10}$aryl; $C_{5-10}$aryl-$C_{1-4}$alkyl; or halogenated $C_{5-10}$aryl-$C_{1-4}$alkyl;
—$R^{2A}$ is independently —H or —$R^{3AA}$;
—$R^{2AA}$ is independently $C_{1-4}$alkyl; $C_{2-4}$alkenyl; halogenated $C_{1-4}$alkyl; $C_{5-10}$aryl; halogenated $C_{5-10}$aryl; $C_{5-10}$aryl-$C_{1-4}$alkyl; or halogenated $C_{5-10}$aryl-$C_{1-4}$alkyl;
—$R^{2B}$ is independently —H or —$R^{3AA}$;
—$R^{2BB}$ is independently $C_{1-4}$alkyl; $C_{2-4}$alkenyl; halogenated $C_{1-4}$alkyl; $C_{5-10}$aryl; halogenated $C_{5-10}$aryl; $C_{5-10}$aryl-$C_{1-4}$alkyl; or halogenated $C_{5-10}$aryl-$C_{1-4}$alkyl;
—$R^{3A}$ is independently —H or —$R^{3AA}$;
—$R^{3AA}$ is independently $C_{1-4}$alkyl; $C_{2-4}$alkenyl; halogenated $C_{1-4}$alkyl; $C_{5-10}$aryl; halogenated $C_{5-10}$aryl; $C_{5-10}$aryl-$C_{1-4}$alkyl; or halogenated $C_{5-10}$aryl-$C_{1-4}$alkyl;
—$R^{3B}$ is independently —H or —$R^{3BB}$;

—$R^{3BB}$ is independently $C_{1-4}$alkyl; $C_{2-4}$alkenyl; halogenated $C_{1-4}$alkyl; $C_{5-10}$aryl; halogenated $C_{5-10}$aryl; $C_{5-10}$aryl-$C_{1-4}$alkyl; or halogenated $C_{5-10}$aryl-$C_{1-4}$alkyl;

—$R^{4A}$ is independently —H or —$R^{4AA}$;

—$R^{4AA}$ is independently $C_{1-4}$alkyl; $C_{2-4}$alkenyl; halogenated $C_{1-4}$alkyl; $C_{5-10}$aryl; halogenated $C_{5-10}$aryl; $C_{5-10}$aryl-$C_{1-4}$alkyl; or halogenated $C_{5-10}$aryl-$C_{1-4}$alkyl;

—$R^{4B}$ is independently —H or —$R^{4BB}$; and

—$R^{4BB}$ is independently $C_{1-4}$alkyl; $C_{2-4}$alkenyl; halogenated $C_{1-4}$alkyl; $C_{5-10}$aryl; halogenated $C_{5-10}$aryl; $C_{5-10}$aryl-$C_{1-4}$alkyl; or halogenated $C_{5-10}$aryl-$C_{1-4}$alkyl.

The present invention also relates to such methods which incorporate one or more additional (subsequent and/or preceding) steps, for example, to prepare compounds of Formula (5) from compounds of Formula (1); to prepare compounds of Formula (6) from compounds of Formula (5); and to prepare compounds of Formula (2) from compounds of Formula (4), as described herein.

Accordingly, in one embodiment, the method further comprises a preceding step of: converting a compound of Formula (4):

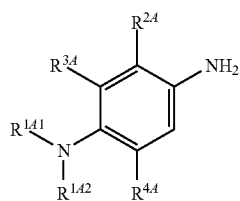

to the corresponding compound of Formula (2):

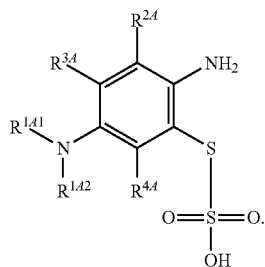

In one embodiment, the method further comprises a subsequent step of: converting the compound of Formula (1):

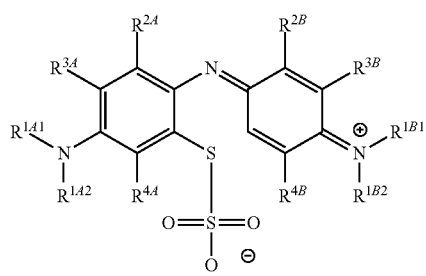

to the corresponding compound of Formula (5):

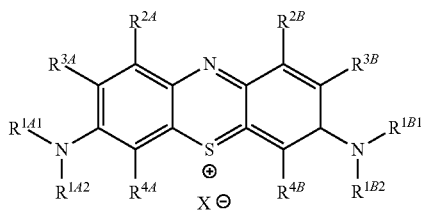

wherein $X^-$ is one or more anionic counter ions to achieve electrical neutrality.

Accordingly, in one embodiment, the method further comprises a subsequent step of: converting the compound of Formula (5):

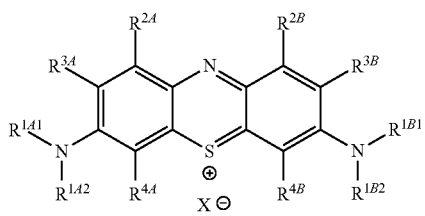

to the corresponding compound of Formula (6):

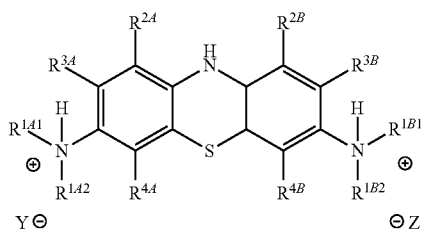

wherein $Y^-$ and $Z^-$, taken together, are one or more anionic counter ions to achieve electrical neutrality.

Another aspect of the present invention pertains to a compound of Formula (1), Formula (5), or Formula (6) as described herein, which is obtainable by a method of synthesis as described herein, or a method comprising a method of synthesis as described herein.

Another aspect of the present invention pertains to a compound of Formula (1), Formula (5), or Formula (6) as described herein, which is obtained by a method of synthesis as described herein, or a method comprising a method of synthesis as described herein.

Another aspect of the present invention pertains to a compound of Formula (5) or Formula (6) as described herein (for example, which is obtainable, or which is obtained by a method as described herein), for use in medicine, for example, for use in treatment or prophylaxis, for example, for use in treatment or prophylaxis of a disorder (e.g., a disease), as described herein.

Another aspect of the present invention pertains to use of a compound of Formula (1), Formula (5), or Formula (6) as described herein (for example, which is obtainable, or which is obtained by a method as described herein), in the manufacture of a medicament, for example, for use in a method of treatment or prophylaxis, for example, for use in a method of treatment or prophylaxis of a disorder (e.g., a disease), as described herein.

Another aspect of the present invention pertains to a method of treatment or prophylaxis, for example, a method of treatment or prophylaxis of a disorder (e.g., a disease), as described herein, comprising administering to a subject in need of treatment a therapeutically-effective amount of a compound of Formula (5) or Formula (6) as described herein (for example, which is obtainable, or which is obtained by a method as described herein) preferably in the form of a pharmaceutical composition.

As will be appreciated by one of skill in the art, features and preferred embodiments of one aspect of the invention will also pertain to other aspects of the invention.

BRIEF DESCRIPTON OF THE DRAWINGS

DETAILED DESCRIPTION OF THE INVENTION

Figure 1:
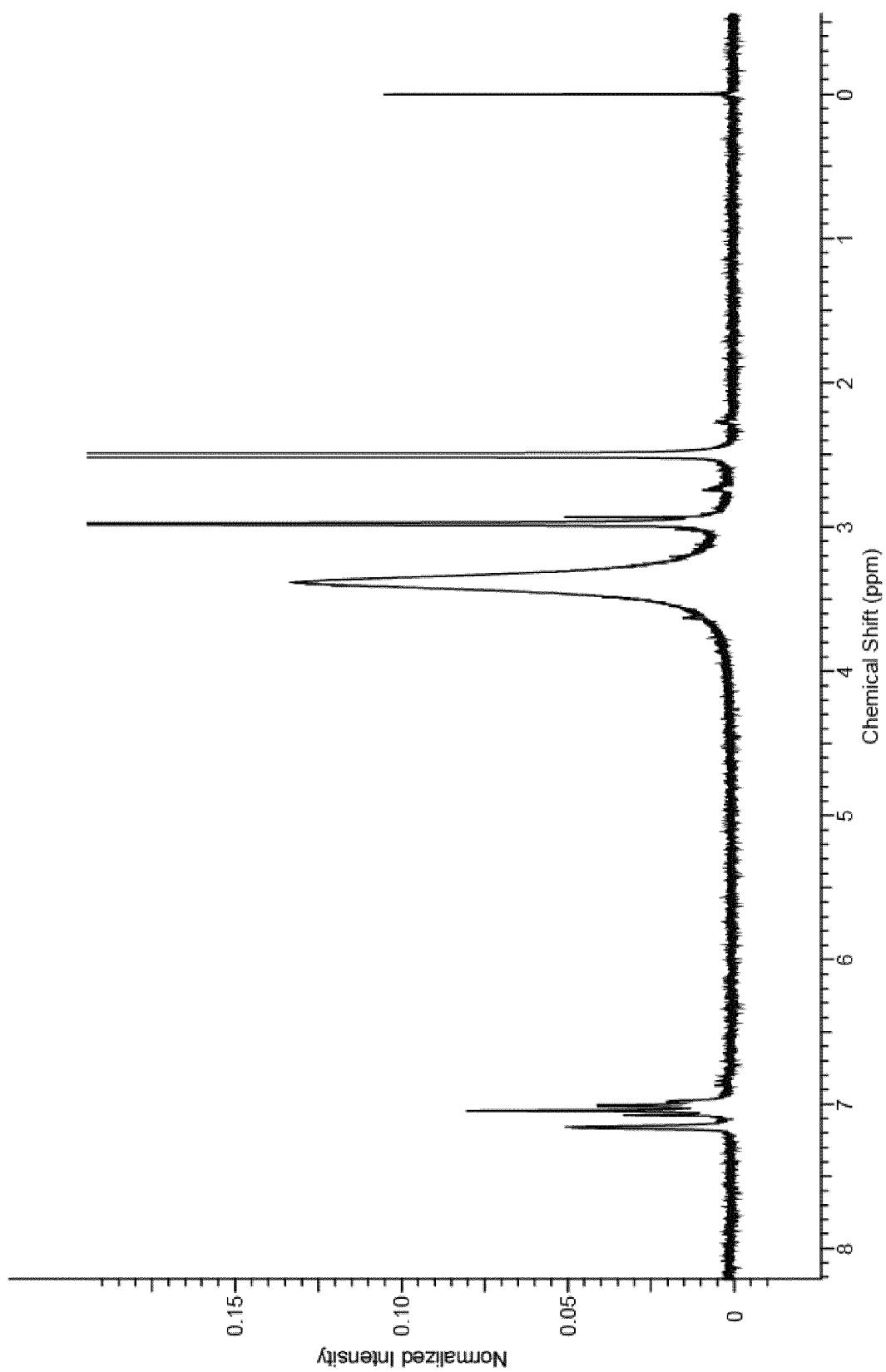
FIG. 1 shows the $^1$H NMR (300 MHz, DMSO-$d_6$) spectrum for thiosulphonic acid S-(2-amino-5-dimethyl amino) phenyl ester obtained in Method 1.

The present invention relates to methods for chemical synthesis which include the step of preparing a thiosulfonic acid of Formula (1) by a step of periodate mediated oxidative coupling of a thiosulfonic acid of Formula (2) and an aniline of Formula (3).

The present invention also relates to such methods which incorporate one or more additional (subsequent and/or preceding) steps, for example: to prepare compounds of Formula (5) from compounds of Formula (1); to prepare compounds of Formula (6) from compounds of Formula (5); and to prepare compounds of Formula (2) from compounds of Formula (4).

These methods, and method steps, are illustrated in the following scheme.

Scheme 1

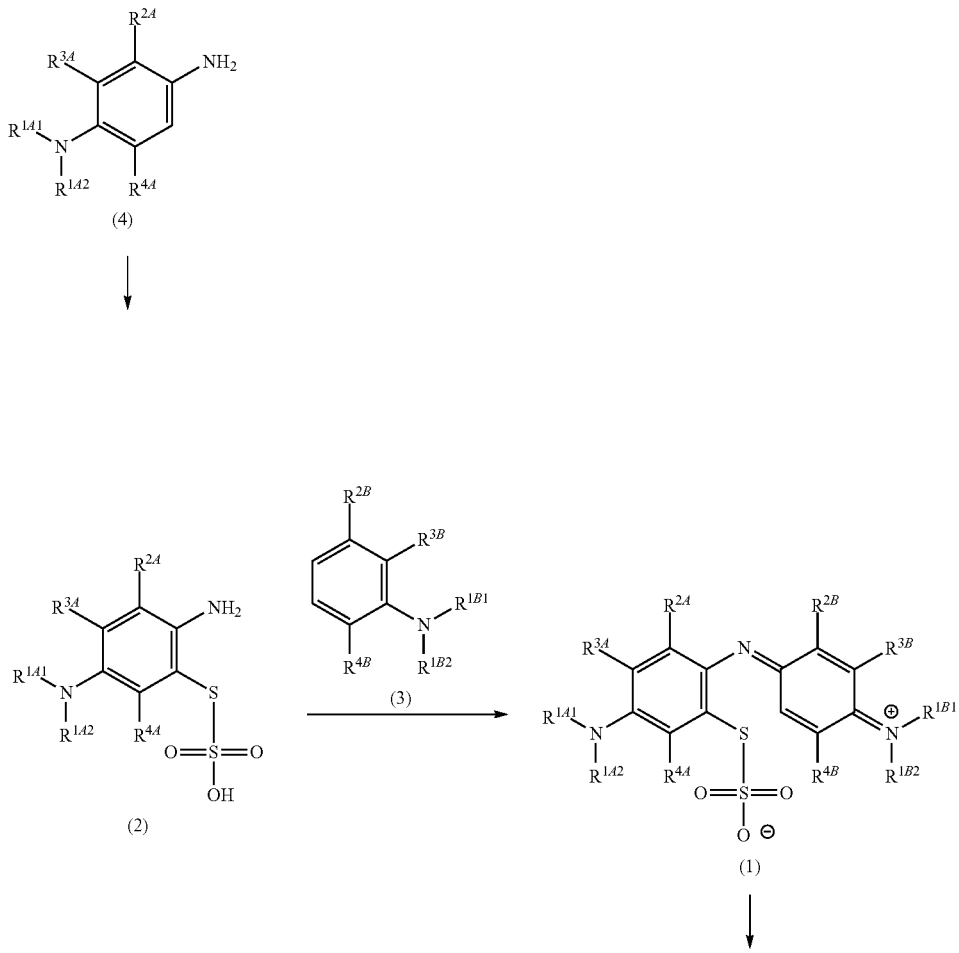

-continued

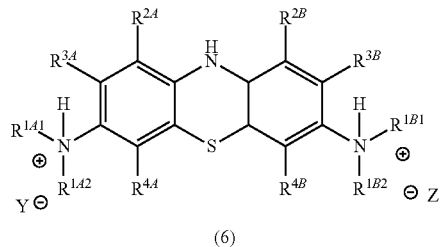

(6)

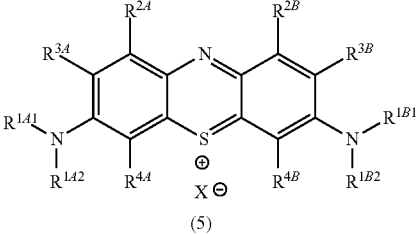

(5)

Accordingly, one aspect of the invention is a method of chemical synthesis of a compound of Formula (1):

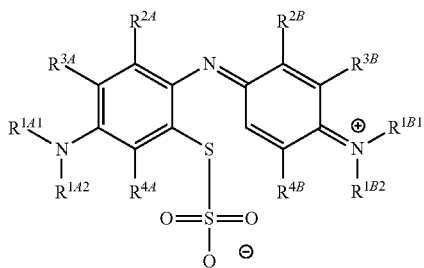

comprising a step of periodate mediated oxidative coupling, in which a compound of Formula (2):

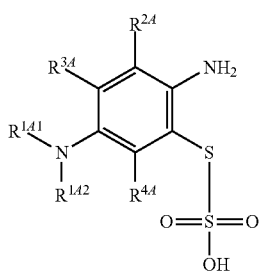

is reacted with a compound of Formula (3):

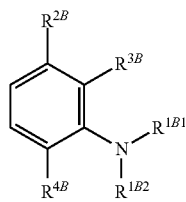

and a periodate oxidising agent;
to form said compound of Formula (1); wherein:
—$R^{1A1}$ is independently $C_{1-4}$alkyl; $C_{2-4}$alkenyl; halogenated $C_{1-4}$alkyl; $C_{5-10}$aryl; halogenated $C_{5-10}$aryl; $C_{5-10}$aryl-$C_{1-4}$alkyl; or halogenated $C_{5-10}$aryl-$C_{1-4}$alkyl;
—$R^{1A2}$ is independently $C_{1-4}$alkyl; $C_{2-4}$alkenyl; halogenated $C_{1-4}$alkyl; $C_{5-10}$aryl; halogenated $C_{5-10}$aryl; $C_{5-10}$aryl-$C_{1-4}$alkyl; or halogenated $C_{5-10}$aryl-$C_{1-4}$alkyl;
—$R^{1B1}$ is independently $C_{1-4}$alkyl; $C_{2-4}$alkenyl; halogenated $C_{1-4}$alkyl; $C_{5-10}$aryl; halogenated $C_{5-10}$aryl; $C_{5-10}$aryl-$C_{1-4}$alkyl; or halogenated $C_{5-10}$aryl-$C_{1-4}$alkyl;
—$R^{1B2}$ is independently $C_{1-4}$alkyl; $C_{2-4}$alkenyl; halogenated $C_{1-4}$alkyl; $C_{5-10}$aryl; halogenated $C_{5-10}$aryl; $C_{5-10}$aryl-$C_{1-4}$alkyl; or halogenated $C_{5-10}$aryl-$C_{1-4}$alkyl;
—$R^{2A}$ is independently —H or —$R^{3AA}$;
—$R^{2AA}$ is independently $C_{1-4}$alkyl; $C_{2-4}$alkenyl; halogenated $C_{1-4}$alkyl; $C_{5-10}$aryl; halogenated $C_{5-10}$aryl; $C_{5-10}$aryl-$C_{1-4}$alkyl; or halogenated $C_{5-10}$aryl-$C_{1-4}$alkyl;
—$R^{2B}$ is independently —H or —$R^{3AA}$;
—$R^{2BB}$ is independently $C_{1-4}$alkyl; $C_{2-4}$alkenyl; halogenated $C_{1-4}$alkyl; $C_{5-10}$aryl; halogenated $C_{5-10}$aryl; $C_{5-10}$aryl-$C_{1-4}$alkyl; or halogenated $C_{5-10}$aryl-$C_{1-4}$alkyl;
—$R^{3A}$ is independently —H or —$R^{3AA}$;
—$R^{3AA}$ is independently $C_{1-4}$alkyl; $C_{2-4}$alkenyl; halogenated $C_{1-4}$alkyl; $C_{5-10}$aryl; halogenated $C_{5-10}$aryl; $C_{5-10}$aryl-$C_{1-4}$alkyl; or halogenated $C_{5-10}$aryl-$C_{1-4}$alkyl;
—$R^{3B}$ is independently —H or —$R^{3BB}$;
—$R^{3BB}$ is independently $C_{1-4}$alkyl; $C_{2-4}$alkenyl; halogenated $C_{1-4}$alkyl; $C_{5-10}$aryl; halogenated $C_{5-10}$aryl; $C_{5-10}$aryl-$C_{1-4}$alkyl; or halogenated $C_{5-10}$aryl-$C_{1-4}$alkyl;
—$R^{4A}$ is independently —H or —$R^{4AA}$;
—$R^{4AA}$ is independently $C_{1-4}$alkyl; $C_{2-4}$alkenyl; halogenated $C_{1-4}$alkyl; $C_{5-10}$aryl; halogenated $C_{5-10}$aryl; $C_{5-10}$aryl-$C_{1-4}$alkyl; or halogenated $C_{5-10}$aryl-$C_{1-4}$alkyl;
—$R^{4B}$ is independently —H or —$R^{4BB}$; and
—$R^{4BB}$ is independently $C_{1-4}$alkyl; $C_{2-4}$alkenyl; halogenated $C_{1-4}$alkyl; $C_{5-10}$aryl; halogenated $C_{5-10}$aryl; $C_{5-10}$aryl-$C_{1-4}$alkyl; or halogenated $C_{5-10}$aryl-$C_{1-4}$alkyl.

Alkyl Groups

In one embodiment, the $C_{1-4}$alkyl groups are selected from: linear $C_{1-4}$alkyl groups, such as —Me, —Et, —nPr, —iPr, and —nBu; branched $C_{3-4}$alkyl groups, such as —iPr, —iBu, —sBu, and —tBu; and cyclic $C_{3-4}$alkyl groups, such as —cPr and —cBu.

Alkenyl Groups

In one embodiment, the $C_{2-4}$alkenyl groups are selected from linear $C_{1-4}$alkenyl groups, such as —CH═CH$_2$ (vinyl) and —CH$_2$—CH═CH$_2$ (allyl).

Halogenated Alkyl Groups

In one embodiment, the halogenated $C_{1-4}$alkyl groups are selected from: —CF$_3$, —CH$_2$CF$_3$, —CH$_2$CH$_2$F, and —CF$_2$CF$_3$.

Aryl Groups

In one embodiment, the $C_{5-10}$aryl groups are selected from: $C_{6-10}$carboaryl groups, such as phenyl and napthyl; and $C_{5-10}$heteroaryl groups, such as thienyl, imidazolyl, pyrazolyl, triazolyl, oxazolyl, isoxazolyl, thiazolyl, isothiazolyl, pyridyl, pyrimidinyl, and quinolinyl.

Halogenated Aryl Groups

In one embodiment, the halogenated $C_{5-10}$aryl groups are selected from: halogenated $C_{6-10}$carboaryl groups, such as 4-fluoro-phenyl, 3-fluoro-phenyl, and 2-fluoro-phenyl, and halogenated $C_{5-10}$heteroaryl groups.

Aryl-Alkyl Groups

In one embodiment, the $C_{5-10}$aryl-$C_{1-4}$alkyl groups are selected from: benzyl and phenethyl.

Halogenated Aryl-Alkyl Groups

In one embodiment, the halogenated $C_{5-10}$aryl-$C_{1-4}$alkyl groups are selected from: halogenated $C_{5-10}$carboaryl-$C_{1-4}$alkyl groups, such as 4-fluoro-benzyl, 3-fluoro-benzyl, and 2-fluoro-benzyl, and halogenated $C_{5-10}$heteroaryl-$C_{1-4}$alkyl groups.

The Group —$R^{1A1}$

In one embodiment, —$R^{1A1}$ is independently $C_{1-4}$alkyl; $C_{2-4}$alkenyl; or halogenated $C_{1-4}$alkyl.

In one embodiment, —$R^{1A1}$ is independently —Me, —Et, —nPr, —nBu, —CH$_2$—CH=CH$_2$, or —CF$_3$.

In one embodiment, —$R^{1A1}$ is independently $C_{1-4}$alkyl; or halogenated $C_{1-4}$alkyl.

In one embodiment, —$R^{1A1}$ is independently —Me, —Et, or —CF$_3$.

In one embodiment, —$R^{1A1}$ is independently $C_{1-4}$alkyl.

In one embodiment, —$R^{1A1}$ is independently —Me or —Et.

In one embodiment, —$R^{1A1}$ is independently —Me.

In one embodiment, —$R^{1A1}$ is independently —Et.

The Group —$R^{1A2}$

In one embodiment, —$R^{1A2}$ is independently $C_{1-4}$alkyl; $C_{2-4}$alkenyl; or halogenated $C_{1-4}$alkyl.

In one embodiment, —$R^{1A2}$ is independently —Me, —Et, —nPr, —nBu, —CH$_2$—CH=CH$_2$, or —CF$_3$.

In one embodiment, —$R^{1A2}$ is independently $C_{1-4}$alkyl; or halogenated $C_{1-4}$alkyl.

In one embodiment, —$R^{1A2}$ is independently —Me, —Et, or —CF$_3$.

In one embodiment, —$R^{1A2}$ is independently $C_{1-4}$alkyl.

In one embodiment, —$R^{1A2}$ is independently —Me or —Et.

In one embodiment, —$R^{1A2}$ is independently —Me.

In one embodiment, —$R^{1A2}$ is independently —Et.

The Groups —$R^{1A1}$ and —$R^{1A2}$

In one embodiment, —$R^{1A1}$ and —$R^{1A2}$ are the same.

In one embodiment, —$R^{1A1}$ and —$R^{1A2}$ are different.

The Group —$R^{1B1}$

In one embodiment, —$R^{1B1}$ is independently $C_{1-4}$alkyl; $C_{2-4}$alkenyl; or halogenated $C_{1-4}$alkyl.

In one embodiment, —$R^{1B1}$ is independently —Me, —Et, —nPr, —nBu, —CH$_2$—CH=CH$_2$, or —CF$_3$.

In one embodiment, —$R^{1B1}$ is independently $C_{1-4}$alkyl; or halogenated $C_{1-4}$alkyl.

In one embodiment, —$R^{1B1}$ is independently —Me, —Et, or —CF$_3$.

In one embodiment, —$R^{1B1}$ is independently $C_{1-4}$alkyl.

In one embodiment, —$R^{1B1}$ is independently —Me or —Et.

In one embodiment, —$R^{1B1}$ is independently —Me.

In one embodiment, —$R^{1B1}$ is independently —Et.

The Group —$R^{1B2}$

In one embodiment, —$R^{1B2}$ is independently $C_{1-4}$alkyl; $C_{2-4}$alkenyl; or halogenated $C_{1-4}$alkyl.

In one embodiment, —$R^{1B2}$ is independently —Me, —Et, —nPr, —nBu, —CH$_2$—CH=CH$_2$, or —CF$_3$.

In one embodiment, —$R^{1B2}$ is independently $C_{1-4}$alkyl; or halogenated $C_{1-4}$alkyl.

In one embodiment, —$R^{1B2}$ is independently —Me, —Et, or —CF$_3$.

In one embodiment, —$R^{1B2}$ is independently $C_{1-4}$alkyl.

In one embodiment, —$R^{1B2}$ is independently —Me or —Et.

In one embodiment, —$R^{1B2}$ is independently —Me.

In one embodiment, —$R^{1B2}$ is independently —Et.

The Groups —$R^{1B1}$ and —$R^{1B2}$

In one embodiment, —$R^{1B1}$ and —$R^{1B2}$ are the same.

In one embodiment, —$R^{1B1}$ and —$R^{1B2}$ are different.

The Groups —$R^{1A1}$, —$R^{1A2}$, —$R^{1B1}$, and —$R^{1B2}$

In one embodiment, —$R^{1A1}$, —$R^{1A2}$, —$R^{1B1}$, and —$R^{1B2}$ are the same.

The Group —$R^{2A}$

In one embodiment, —$R^{2A}$ is independently —H.

In one embodiment, —$R^{2A}$ is independently —$R^{2AA}$.

The Group —$R^{2AA}$

In one embodiment, —$R^{2AA}$, if present, is independently $C_{1-4}$alkyl; $C_{2-4}$alkenyl; or halogenated $C_{1-4}$alkyl.

In one embodiment, —$R^{2AA}$, if present, is independently $C_{1-4}$alkyl; or halogenated $C_{1-4}$alkyl.

In one embodiment, —$R^{2AA}$, if present, is independently —Me, —Et, or —CF$_3$.

In one embodiment, —$R^{2AA}$, if present, is independently $C_{1-4}$alkyl.

In one embodiment, —$R^{2AA}$, if present, is independently —Me or —Et.

In one embodiment, —$R^{2AA}$, if present, is independently —Me.

In one embodiment, —$R^{2AA}$, if present, is independently —Et.

The Group —$R^{2B}$

In one embodiment, —$R^{2B}$ is independently —H.

In one embodiment, —$R^2B$ is independently —$R^{2BB}$.

The Group —$R^{2BB}$

In one embodiment, —$R^{2BB}$, if present, is independently $C_{1-4}$alkyl; $C_{2-4}$alkenyl; or halogenated $C_{1-4}$alkyl.

In one embodiment, —$R^{2BB}$, if present, is independently $C_{1-4}$alkyl; or halogenated $C_{1-4}$alkyl.

In one embodiment, —$R^{2BB}$, if present, is independently —Me, —Et, or —CF$_3$.

In one embodiment, —$R^{2BB}$, if present, is independently $C_{1-4}$alkyl.

In one embodiment, —$R^{2BB}$, if present, is independently —Me or —Et.

In one embodiment, —$R^{2BB}$, if present, is independently —Me.

In one embodiment, —$R^{2BB}$, if present, is independently —Et.

The Groups —$R^{2A}$ and —$R^{2B}$

In one embodiment, —$R^{2A}$ and —$R^{2B}$ are the same.

In one embodiment, —$R^{2A}$ and —$R^{2B}$ are different.

The Group —$R^{3A}$

In one embodiment, —$R^{3A}$ is independently —H.

In one embodiment, —$R^{3A}$ is independently —$R^{3AA}$.

The Group —$R^{3AA}$

In one embodiment, —$R^{3AA}$, if present, is independently $C_{1-4}$alkyl; $C_{2-4}$alkenyl; or halogenated $C_{1-4}$alkyl.

In one embodiment, —$R^{3AA}$, if present, is independently $C_{1-4}$alkyl; or halogenated $C_{1-4}$alkyl.

In one embodiment, —$R^{3AA}$, if present, is independently —Me, —Et, or —CF$_3$.

In one embodiment, —$R^{3AA}$, if present, is independently $C_{1-4}$alkyl.

In one embodiment, —$R^{3AA}$, if present, is independently —Me or —Et.

In one embodiment, —$R^{3AA}$, if present, is independently —Me.

In one embodiment, —$R^{3AA}$, if present, is independently —Et.

The Group —$R^{3B}$

In one embodiment, —$R^{3B}$ is independently —H.

In one embodiment, —$R^3B$ is independently —$R^{3BB}$.

The Group —$R^{3BB}$

In one embodiment, —$R^{3BB}$, if present, is independently $C_{1-4}$alkyl; $C_{2-4}$alkenyl; or halogenated $C_{1-4}$alkyl.

In one embodiment, —$R^{3BB}$, if present, is independently $C_{1-4}$alkyl; or halogenated $C_{1-4}$alkyl.

In one embodiment, —$R^{3BB}$, if present, is independently —Me, —Et, or —$CF_3$.

In one embodiment, —$R^{3BB}$, if present, is independently $C_{1-4}$alkyl.

In one embodiment, —$R^{3BB}$, if present, is independently —Me or —Et.

In one embodiment, —$R^{3BB}$, if present, is independently —Me.

In one embodiment, —$R^{3BB}$, if present, is independently —Et.

The Groups —$R^{3A}$ and —$R^{3B}$

In one embodiment, —$R^{3A}$ and —$R^{3B}$ are the same.

In one embodiment, —$R^{3A}$ and —$R^{3B}$ are different.

The Group —$R^{4A}$

In one embodiment, —$R^{4A}$ is independently —H.

In one embodiment, —$R^{4A}$ is independently —$R^{4AA}$.

The Group —$R^{4AA}$

In one embodiment, —$R^{4AA}$, if present, is independently $C_{1-4}$alkyl; $C_{2-4}$alkenyl; or halogenated $C_{1-4}$alkyl.

In one embodiment, —$R^{4AA}$, if present, is independently $C_{1-4}$alkyl; or halogenated $C_{1-4}$alkyl.

In one embodiment, —$R^{4AA}$, if present, is independently —Me, —Et, or —$CF_3$.

In one embodiment, —$R^{4AA}$, if present, is independently $C_{1-4}$alkyl.

In one embodiment, —$R^{4AA}$, if present, is independently —Me or —Et.

In one embodiment, —$R^{4AA}$, if present, is independently —Me.

In one embodiment, —$R^{4AA}$, if present, is independently —Et.

The Group —$R^{4B}$

In one embodiment, —$R^{4B}$ is independently —H.

In one embodiment, —$R^{4B}$ is independently —$R^{4BB}$.

The Group —$R^{4BB}$

In one embodiment, —$R^{4BB}$, if present, is independently $C_{1-4}$alkyl; $C_{2-4}$alkenyl; or halogenated $C_{1-4}$alkyl.

In one embodiment, —$R^{4BB}$, if present, is independently $C_{1-4}$alkyl; or halogenated $C_{1-4}$alkyl.

In one embodiment, —$R^{4BB}$, if present, is independently —Me, —Et, or —$CF_3$.

In one embodiment, —$R^{4BB}$, if present, is independently $C_{1-4}$alkyl.

In one embodiment, —$R^{4BB}$, if present, is independently —Me or —Et.

In one embodiment, —$R^{4BB}$, if present, is independently —Me.

In one embodiment, —$R^{4BB}$, if present, is independently —Et.

The Groups —$R^{4A}$ and —$R^{4B}$

In one embodiment, —$R^{4A}$ and —$R^{4B}$ are the same.

In one embodiment, —$R^{4A}$ and —$R^{4B}$ are different.

Combinations

It is appreciated that certain features of the invention, which are, for clarity, described in the context of separate embodiments, may also be provided in combination in a single embodiment. Conversely, various features of the invention, which are, for brevity, described in the context of a single embodiment, may also be provided separately or in any suitable sub-combination. All combinations of the embodiments pertaining to the chemical groups represented by variables (e.g., —$R^{1A1}$, —$R^{1A2}$, —$R^{1B1}$, —$R^{1B2}$, —$R^{2A}$, —$R^{2AA}$, —$R^{2B}$, —$R^{2BB}$, —$R^{3A}$, —$R^{3AA}$, —$R^{3B}$, —$R^{3BB}$, —$R^{4A}$, —$R^{4AA}$, —$R^{4B}$, —$R^{4BB}$, $X^-$, $Y^-$, and $Z^-$, etc.) are specifically embraced by the present invention and are disclosed herein just as if each and every combination was individually and explicitly disclosed, to the extent that such combinations embrace compounds that are stable compounds (i.e., compounds that can be isolated, characterised, and tested). In addition, all sub-combinations of the chemical groups listed in the embodiments describing such variables are also specifically embraced by the present invention and are disclosed herein just as if each and every such sub-combination of chemical groups was individually and explicitly disclosed herein.

Periodate Oxidising Agent

The periodate oxidizing agent is an iodine oxyanion that is able to facilitate periodate mediated oxidative coupling, specifically, the coupling of a compound of Formula (2) and a compound of Formula (3).

Iodine oxyanions include iodine peroxides, for example, periodic acid and periodate salts.

Periodic acid may be provided, for example, as $HIO_4$, $H_4I_2O_9$ (e.g., $2HIO_4$ plus $H_2O$), or $H_5IO_6$ (e.g., $HIO_4$ plus $2H_2O$).

Periodate salts include alkali metal salts, such as sodium salts, such as $NaH_4IO_6$ (e.g., $NaIO_4$ plus $2H_2O$), $Na_2H_3IO_6$ (e.g., $NaIO_4$ plus $NaOH$ plus $H_2O$), and $Na_3H_2IO_6$ (e.g., $NaIO_4$ plus $2NaOH$); potassium salts, such as $KIO_4$; and cesium salts, such as $CsIO_4$.

In one embodiment, the periodate oxidizing agent is an iodine peroxide.

In one embodiment, the periodate oxidizing agent is periodic acid or a periodate salt.

In one embodiment, the periodate oxidizing agent is periodic acid.

In one embodiment, the periodate oxidizing agent is a periodate salt.

In one embodiment, the periodate oxidizing agent is an alkali metal periodate salt.

In one embodiment, the periodate oxidizing agent is a sodium periodate salt.

In one embodiment, the periodate oxidizing agent is sodium periodate ($NaIO_4$).

The Reaction Step of Periodate Mediated Oxidative Coupling

The periodate mediated oxidative coupling, specifically, the coupling of a compound of Formula (2) and a compound of Formula (3) using a periodate oxidizing agent, is performed under conditions suitable to achieve coupling to form a compound of Formula (1).

In one embodiment, the ratio, A, of the amount of compound of Formula (2), in equivalents, to the amount of compound of Formula (3), in equivalents, is from about 0.5 to about 3.0.

In one embodiment, the range is from about 0.6 to about 2.0.

In one embodiment, the range is from about 0.7 to about 1.5.

In one embodiment, the range is from about 0.8 to about 1.2.

In one embodiment, the range is from about 0.9 to about 1.1.

In one embodiment, the ratio is about 1.

As an illustration, in one example of the periodate mediated oxidative coupling, thiosulphonic acid S-(2-amino-5-dimethyl amino) phenyl ester (5.92 g, 248.32 g/mol, 23.8 mmol, 1.0 equivalent) (a compound of Formula (2)) is reacted with N,N-dimethylaniline ($C_6H_5N(CH_3)_2$, 2.89 g, 121.18 g/mol, 23.8 mmol, 1.0 equivalent) (a compound of Formula (3)).

In another example of the periodate mediated oxidative coupling, thiosulphonic acid S-(2-amino-5-dimethyl amino) phenyl ester (10.0 g, 248.32 g/mol, 40.3 mmol, 1.0 equivalent) (a compound of Formula (2)) is reacted with N,N-dimethylaniline ($C_6H_5N(CH_3)_2$, 4.88 g, 121.18 g/mol, 40.3 mmol, 1.0 equivalent) (a compound of Formula (3)).

In one embodiment, the ratio, B, of the amount of compound of Formula (2), in equivalents, to the amount of compound of periodate oxidizing agent, in equivalents, is from about 0.5 to about 3.0.

In one embodiment, the range is from about 1.0 to about 3.0.

In one embodiment, the range is from about 1.5 to about 2.5.

In one embodiment, the range is from about 1.8 to about 2.3.

In one embodiment, the range is from about 1.9 to about 2.2.

In one embodiment, the range is from about 2.0 to about 2.2.

In one embodiment, the ratio is about 2.1.

As an illustration, in one example of the periodate mediated oxidative coupling, thiosulphonic acid S-(2-amino-5-dimethyl amino) phenyl ester (5.92 g, 248.32 g/mol, 23.8 mmol, 1.0 equivalent) (a compound of Formula (2)) is reacted with sodium periodate ($NaIO_4$, 10.66 g, 213.89 g/mol, 49.8 mmol, 2.09 equivalents) (a periodate oxidizing agent).

In another example of the periodate mediated oxidative coupling, thiosulphonic acid S-(2-amino-5-dimethyl amino) phenyl ester (10.0 g, 248.32 g/mol, 40.3 mmol, 1.0 equivalent) (a compound of Formula (2)) is reacted with sodium periodate ($NaIO_4$, 17.67 g, 213.89 g/mol, 82.6 mmol, 2.05 equivalents).

In one embodiment, the reaction is carried out at a temperature of from about 0° C. to about 30° C.

In one embodiment, the range is from about 1° C. to about 20° C.

In one embodiment, the range is from about 1° C. to about 15° C.

In one embodiment, the range is from about 1° C. to about 10° C.

In one embodiment, the range is from about 1° C. to about 8° C.

In one embodiment, the range is from about 1° C. to about 8° C.

In one embodiment, the range is from about 2° C. to about 20° C.

In one embodiment, the range is from about 2° C. to about 15° C.

In one embodiment, the range is from about 2° C. to about 10° C.

In one embodiment, the range is from about 2° C. to about 8° C.

In one embodiment, the range is from about 2° C. to about 8° C.

In one embodiment, the temperature is about 5° C.

In one embodiment, the reaction time is from about 5 minutes to about 12 hours.

In one embodiment, the range is from about 10 minutes to about 12 hours.

In one embodiment, the range is from about 15 minutes to about 6 hours.

In one embodiment, the range is from about 30 minutes to about 4 hours.

In one embodiment, the range is from about 1 hour to about 3 hours.

In one embodiment, the time is about 2 hours.

In one embodiment, the reaction is carried out in the presence of an acid.

In one embodiment, the reaction is carried out in the presence of a strong acid.

In one embodiment, the reaction is carried out in the presence of sulfuric acid.

In one embodiment, the reaction is carried out in the presence of concentrated sulfuric acid.

In one embodiment, when the reaction is carried out in the presence of an acid, the ratio, C, of the amount of compound of Formula (2), in equivalents, to the amount of $H^+$ provided by the acid, in equivalents, is from about 0.5 to about 3.0.

In one embodiment, the range is from about 0.6 to about 2.0.

In one embodiment, the range is from about 0.7 to about 1.5.

In one embodiment, the range is from about 0.8 to about 1.2.

In one embodiment, the range is from about 0.9 to about 1.1.

In one embodiment, the ratio is about 1.

In some embodiments, the acid is a strong diprotic acid, for example sulphuric acid, so that 0.5 equivalents of strong diprotic acid corresponds to 1.0 equivalents of $H^+$.

As an illustration, in one example of the periodate mediated oxidative coupling, thiosulphonic acid S-(2-amino-5-dimethyl amino) phenyl ester (5.92 g, 248.32 g/mol, 23.8 mmol, 1.0 equivalent) (a compound of Formula (2)) is used in the presence of sulphuric acid ($H_2SO_4$, 98%, 1.17 g, 98.08 g/mol, 11.9 mmol, 0.5 equivalents of $H_2SO_4$, 1.0 equivalents of $H^+$).

In another example of the periodate mediated oxidative coupling, thiosulphonic acid S-(2-amino-5-dimethyl amino) phenyl ester (10.0 g, 248.32 g/mol, 40.3 mmol, 1.0 equivalent) (a compound of Formula (2)) is used in the presence of sulphuric acid ($H_2SO_4$, 98%, 1.97 g, 98.08 g/mol, 20.1 mmol, 0.5 equivalents of $H_2SO_4$, 1.0 equivalents of $H^+$).

In one embodiment, the reaction is carried out in the presence of water.

In one embodiment, the acid is added to the compound of Formula (3) in water; then the compound of Formula (4) is added; and then the periodate oxidizing agent is added.

In one embodiment, the acid is added stepwise.

In one embodiment, the compound of Formula (4) is added in one aliquot.

In one embodiment, the periodate oxidizing agent is added stepwise.

Additional Steps

The present invention also relates to such methods which incorporate one or more additional (subsequent and/or preceding) steps, for example: to prepare compounds of Formula (5) from compounds of Formula (1); to prepare compounds of Formula (6) from compounds of Formula (5); and to prepare compounds of Formula (2) from compounds of Formula (4), as described herein.

Preceding Step: Thiosulfonic Acid Formation

In one embodiment, the methods described above further comprise a preceding step of: converting a compound of Formula (4):

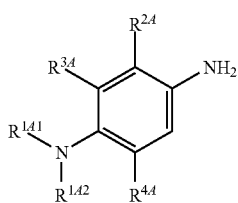

to the corresponding compound of Formula (2):

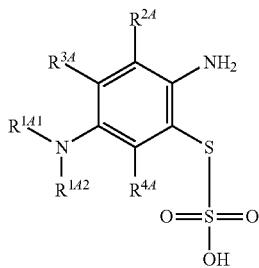

wherein each of —$R^{1A1}$, —$R^{1A2}$, —$R^{2A}$, —$R^{3A}$ and —$R^{4A}$ is as defined herein.

Methods, reagents, and reaction conditions suitable for such a reaction are well known in the art. See, for example, WO 2010/130977 A1 (WisTa Laboratories Ltd., 18 Nov. 2010). In particular, see: Synthesis 1, examples 1 to 6, pages 55 to 59; Synthesis 4, page 61; Synthesis 5, page 62; and Synthesis 6, example 1 page 66-67 and example 2 page 68.

For example, the compound of Formula (4) may be reacted with aluminium sulphate hexdecahydrate, then sodium thiosulphate, and then potassium persulphate, in water, at a temperature of about 5-15° C., and stirred for about 2 hours; and the precipitate collected, washed, and dried.

Subsequent Step: Cyclization

In one embodiment, the methods described above further comprise a subsequent step of: converting the compound of Formula (1):

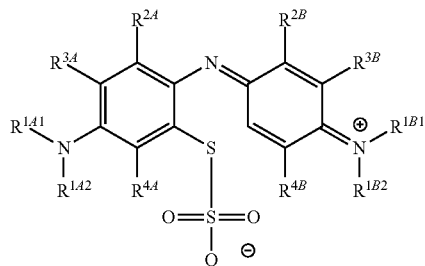

to the corresponding compound of Formula (5):

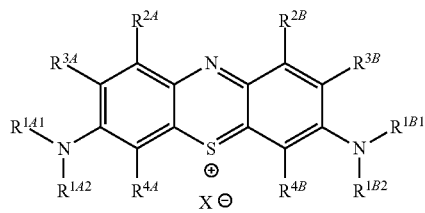

wherein each of —$R^{1A1}$, —$R^{1A2}$, —$R^{1B1}$, —$R^{1B2}$, —$R^{2A}$, —$R^{2B}$, —$R^{3A}$, —$R^{3B}$, —$R^{4A}$, and —$R^{4B}$ is as defined herein; and wherein $X^-$ is independently one or more anionic counter ions to achieve electrical neutrality.

In one embodiment, $X^-$ is independently a counter anion to achieve electrical neutrality.

In one embodiment, $X^-$ is independently a counter anion shared with one or more other cations (e.g., the cation shown in Formula (5)) to achieve electrical neutrality.

In one embodiment, $X^-$ is independently a halogen anion (i.e., a halide).

In one embodiment, $X^-$ is independently $F^-$, $Cl^-$, $Br^-$, or $I^-$.

In one embodiment, $X^-$ is independently $Cl^-$, $Br^-$, or $I^-$.

In one embodiment, $X^-$ is independently $Cl^-$.

In one embodiment, $X^-$ is independently $NO_3^-$ (nitrate).

In one embodiment, $X^-$ is independently $ClO_3^-$ (perchlorate).

In one embodiment, $X^-$ is independently $S_2O_8^-$ (persulfate).

In one embodiment, $X^-$ is independently formate, propionate, or benzoate.

In one embodiment, $X^-$ is independently 4-hydroxybenzenesulfonate, p-toluenesulfonate ($CH_3$—$C_6H_4$—$S(=O)_2O^-$), or methylsulfonate ($CH_3S(=O)_2O^-$).

In one embodiment, $X^-$ is independently derived from $FeCl_3$ or $ZnCl_2$.

In one embodiment, $X^-$ is independently $SO_4^{-2}$ (sulfate).

In one embodiment, $X^-$ is independently succinate.

In one embodiment, $X^-$ is independently citrate (and, e.g., is shared with one or more other cations (e.g., the cation shown in Formula (6)) to achieve electrical neutrality).

Methods, reagents, and reaction conditions suitable for such a reaction are well known in the art. See, for example, WO 2010/130977 A1 (WisTa Laboratories Ltd., 18 Nov. 2010), in particular: Synthesis 3, page 60; Synthesis 5, page 63 to 64; Synthesis 6, page 68-69; and Synthesis 7, page 70. Also see, for example WO 2015/052496 A1 (WisTa Laboratories Ltd., 16 Apr. 2015), in particular see examples 1 to 5, pages 47 to 57.

For example, the compound of Formula (1) may be reacted with copper (II) sulfate, in water, at a temperature of about 85° C. for about 1 hour; the liquid phase collected and reacted with hydrochloric acid and allowed to cool; and the precipitate collected, washed, and dried.

Subsequent Step: Reduction

In one embodiment, the methods described above further comprise a subsequent step of: converting the compound of Formula (5):

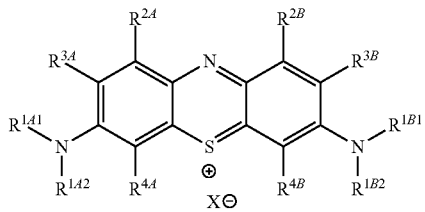

to the corresponding compound of Formula (6):

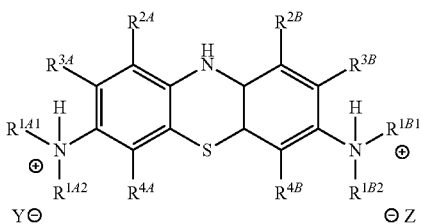

wherein each of —$R^{1A1}$, —$R^{1A2}$, —$R^{1B1}$, —$R^{1B2}$, —$R^{2A}$, —$R^{2B}$, —$R^{3A}$, —$R^{3B}$, —$R^{4A}$, —$R^{4B}$, and $X^-$ is as defined herein; and wherein $Y^-$ and $Z^-$, taken together, are independently one or more anionic counter ions to achieve electrical neutrality.

In one embodiment, $Y^-$ and $Z^-$, taken together, are independently two counter anions to achieve electrical neutrality.

In one embodiment, $Y^-$ and $Z^-$, taken together, is independently one counter anion to achieve electrical neutrality.

In one embodiment, $Y^-$ and $Z^-$, taken together, is independently a counter anion shared with one or more other cations (e.g., the cation shown in Formula (6)) to achieve electrical neutrality.

In one embodiment, each of $Y^-$ and $Z^-$ is independently a halogen anion (i.e., a halide).

In one embodiment, each of $Y^-$ and $Z^-$ is independently $F^-$, $Cl^-$, $Br^-$, or $I^-$.

In one embodiment, each of $Y^-$ and $Z^-$ is independently $Cl^-$, $Br^-$, or $I^-$.

In one embodiment, each of $Y^-$ and $Z^-$ is independently $Cl^-$.

In one embodiment, each of $Y^-$ and $Z^-$ is independently $NO_3^-$ (nitrate).

In one embodiment, each of $Y^-$ and $Z^-$ is independently $ClO_3^-$ (perchlorate).

In one embodiment, each of $Y^-$ and $Z^-$ is independently $S_2O_8^-$ (persulfate).

In one embodiment, each of $Y^-$ and $Z^-$ is independently formate, propionate, or benzoate.

In one embodiment, each of $Y^-$ and $Z^-$ is independently 4-hydroxybenzenesulfonate, p-toluenesulfonate ($CH_3$—$C_6H_4$—$S(=O)_2O^-$), methylsulfonate ($CH_3S(=O)_2O^-$).

In one embodiment, $Y^-$ and $Z^-$, taken together, is independently $SO_4^{-2}$ (sulfate).

In one embodiment, $Y^-$ and $Z^-$, taken together, is independently succinate.

In one embodiment, $Y^-$ and $Z^-$, taken together, is independently citrate (and, e.g., is shared with one or more other cations (e.g., the cation shown in Formula (6)) to achieve electrical neutrality).

Methods, reagents, and reaction conditions suitable for such a reaction are well known in the art. See, for example WO 2007/110627 A2 (WisTa Laboratories Ltd., 4 Oct. 2007), in particular see Synthesis 8 and 9, page 57; Synthesis 12 to 18 and 23, pages 59 to 63 and 65; and Synthesis 20 to 22 pages 64 and 65. See also, for example, PCT/EP2016/067302, WO 2017/013137 (WisTa Laboratories Ltd., filed 20 Jul. 2016), in particular: Method 4, part 3, page 97; and Methods 8 to 12, page 111 to 113.

For example, the compound of Formula (5) may be treated with an acid such as hydrochloric acid in methanol and allowed to stir for 3 hours; the solution is filtered through Celite, washed with methanol and concentrated to provide a compound of Formula (6). Alternatively, for example, the compound of Formula (5) may be treated with an acid such as methane sulfonic acid in methanol and toluene; the mixture is subsequently cooled to 5° C. before ethanol is added such that the product, Formula (6), precipitates and can be collected by filtration.

For example, the compound of Formula (5) may be treated with an acylating agent, such as acetic anhydride, under basic conditions and stirred for 2 hours at around 90° C. to acylate the aromatic nitrogen. The acylated intermediate may then be treated with an acid, such hydrochloric acid, under heating, for example at 80° C. to give the product, Formula (6).

Chemical Synthesis

Methods for the chemical synthesis of compounds of the present invention are described herein. These and/or other well-known methods may be modified and/or adapted in known ways in order to facilitate the synthesis of additional compounds within the scope of the present invention.

Descriptions of general laboratory methods and procedures, useful for the preparation of the compounds described herein, are provided in *Vogel's Textbook of Practical Organic Chemistry*, 5th Edition, 1989, (Editors: Furniss, Hannaford, Smith, and Tatchell) (published by Longmann, UK).

Compositions

One aspect of the present invention pertains to a composition comprising a compound of Formula (1), Formula (5), or Formula (6) as described herein (for example, which is obtainable, or which is obtained by a method as described herein), and a carrier, diluent, or excipient.

Another aspect of the present invention pertains to a method of preparing a composition comprising mixing a compound of Formula (1), Formula (5), or Formula (6) as described herein (for example, which is obtainable, or which is obtained by a method as described herein), and a carrier, diluent, or excipient.

One aspect of the present invention pertains to a pharmaceutical composition comprising a compound of Formula (5) or Formula (6) as described herein (for example, which is obtainable, or which is obtained by a method as described herein), and a pharmaceutically acceptable carrier, diluent, or excipient.

Another aspect of the present invention pertains to a method of preparing a pharmaceutical composition comprising mixing a compound of Formula (5) or Formula (6) as described herein(for example, which is obtainable, or which is obtained by a method as described herein), and a pharmaceutically acceptable carrier, diluent, or excipient.

Uses

The compounds of Formula (5) and Formula (6) as described herein, are useful in medicine (e.g., therapy), for example, in treatment or prophylaxis.

Use in Methods of Therapy

One aspect of the present invention pertains to a compound of Formula (5) or Formula (6) as described herein (for example, which is obtainable, or which is obtained by a method as described herein), for use in medicine, for example, for use in treatment or prophylaxis, for example, for use in treatment or prophylaxis a disorder (e.g., a disease), as described herein.

Use in the Manufacture of Medicaments

One aspect of the present invention pertains to use of a compound of Formula (1), Formula (5), or Formula (6) as described herein (for example, which is obtainable, or which is obtained by a method as described herein), in the manufacture of a medicament, for example, for use in a method of treatment or prophylaxis, for example, for use in a method of treatment or prophylaxis of a disorder (e.g., a disease), as described herein.

In one embodiment, the medicament comprises the compound of Formula (5) or Formula (6).

Methods of Treatment

One aspect of the present invention pertains to a method of treatment or prophylaxis, for example, a method of treatment or prophylaxis of a disorder (e.g., a disease), as described herein, comprising administering to a subject in need of treatment a therapeutically-effective amount of a compound of Formula (5) or Formula (6) as described herein (for example, which is obtainable, or which is obtained by a method as described herein), preferably in the form of a pharmaceutical composition.

Disorders Treated

In one embodiment, the disorder is a disease of protein aggregation.

In one embodiment, the disorder is a tauopathy.

In one embodiment, the disorder is Alzheimer's disease (AD), Pick's disease, progressive supranuclear palsy (PSP), frontotemporal dementia (FTD), FTD with parkinsonism linked to chromosome 17 (FTDP 17), frontotemporal lobar degeneration (FTLD) syndromes; disinhibition-dementia-parkinsonism-amyotrophy complex (DDPAC), pallido-ponto-nigral degeneration (PPND), amyotropic lateral sclerosis (ALS), Guam-ALS syndrome, pallido nigro luysian degeneration (PNLD), cortico-basal degeneration (CBD), dementia with argyrophilic grains (AgD), dementia pugilistica (DP) or chronic traumatic encephalopathy (CTE), Down's syndrome (DS), dementia with Lewy bodies (DLB), subacute sclerosing panencephalitis (SSPE), MCl, Niemann-Pick disease, type C (NPC), Sanfilippo syndrome type B (or mucopolysaccharidosis III B (MPS III B)), or myotonic dystrophies (DM), DM1 or DM2.

In one embodiment, the disorder is Alzheimer's disease.

In one embodiment, the disorder is Parkinson's disease.

In one embodiment, the disorder is PSP, ALS, or FTLD.

In one embodiment, the disorder is Huntington's disease.

In one embodiment, the disorder is Huntington's disease or another polyglutamine disorder, such as spinal bulbar muscular atrophy (Kennedy disease), dentatorubropallidoluysian atrophy, or spinocerebellar ataxias.

In one embodiment, the disorder is skin cancer.

In one embodiment, the disorder is melanoma.

In one embodiment, the disorder is a bacterial, viral, or protozoal disease condition.

In one embodiment, the disorder is a viral disease condition.

In one embodiment, the disorder is Hepatitis C, HIV, or West Nile Virus (WNV) infection.

In one embodiment, the disorder is a protozoan disease.

In one embodiment, the disorder is malaria.

Treatment

The term "treatment," as used herein in the context of treating a disorder, pertains generally to treatment of a human or an animal (e.g., in veterinary applications), in which some desired therapeutic effect is achieved, for example, the inhibition of the progress of the disorder, and includes a reduction in the rate of progress, a halt in the rate of progress, alleviation of symptoms of the disorder, amelioration of the disorder, and cure of the disorder. Treatment as a prophylactic measure (i.e., prophylaxis) is also included. For example, use with patients who have not yet developed the disorder, but who are at risk of developing the disorder, is encompassed by the term "treatment."

The term "therapeutically-effective amount," as used herein, pertains to that amount of a compound, or a material, composition or dosage form comprising a compound, which is effective for producing some desired therapeutic effect, commensurate with a reasonable benefit/risk ratio, when administered in accordance with a desired treatment regimen.

Combination Therapies

The term "treatment" includes combination treatments and therapies, in which two or more treatments or therapies are combined, for example, sequentially or simultaneously. For example, the compounds described herein may also be used in combination therapies, e.g., in conjunction with other agents.

The particular combination would be at the discretion of the physician who would select dosages using his common general knowledge and dosing regimens known to a skilled practitioner.

The agents (i.e., the compound of Formula (1), Formula (2), Formula (5), or Formula (6) plus one or more other agents) may be administered simultaneously or sequentially, and may be administered in individually varying dose schedules and via different routes.

The agents (i.e., the compound of Formula (1), Formula (2), Formula (5), or Formula (6) plus one or more other agents) may be formulated together in a single dosage form, or alternatively, the individual agents may be formulated separately and presented together in the form of a kit, optionally with instructions for their use.

Kits

One aspect of the invention pertains to a kit comprising (a) a compound of Formula (5) or Formula (6) as described herein (for example, which is obtainable, or which is obtained by a method as described herein), or a composition comprising a compound of Formula (5) or Formula (6) as described herein (for example, which is obtainable, or which is obtained by a method as described herein), e.g., preferably provided in a suitable container and/or with suitable packaging; and (b) instructions for use, e.g., written instructions on how to administer the compound or composition.

The written instructions may also include a list of indications for which the active ingredient is a suitable treatment.

Routes of Administration

The compound of Formula (5) or Formula (6) or pharmaceutical composition comprising the compound, may be administered to a subject by any convenient route of administration. Typically, the compound is administered orally or intravenously.

The Subject/Patient

The subject/patient may be a mammal, a placental mammal, a marsupial (e.g., kangaroo, wombat), a rodent (e.g., a guinea pig, a hamster, a rat, a mouse), murine (e.g., a mouse), a lagomorph (e.g., a rabbit), avian (e.g., a bird), canine (e.g., a dog), feline (e.g., a cat), equine (e.g., a horse), porcine (e.g., a pig), ovine (e.g., a sheep), bovine (e.g., a cow), a primate, simian (e.g., a monkey or ape), a monkey (e.g., marmoset, baboon), an ape (e.g., gorilla, chimpanzee, orangutang, gibbon), or a human.

In one preferred embodiment, the subject/patient is a human.

Formulations

While it is possible for a compound of Formula (5) or Formula (6) to be administered alone, it is preferable to present it as a pharmaceutical formulation (e.g., composition, preparation, medicament) comprising at least one compound, as described herein, together with one or more other pharmaceutically acceptable ingredients well-known to those skilled in the art, including pharmaceutically acceptable carriers, diluents, excipients, adjuvants, fillers, buffers, preservatives, anti-oxidants, lubricants, stabilisers, solubilisers, surfactants (e.g., wetting agents), masking agents, colouring agents, flavouring agents, and sweetening agents. If formulated as discrete units (e.g., tablets, etc.), each unit contains a predetermined amount (dosage) of the compound. The formulation may further comprise other active agents, for example, other therapeutic or prophylactic agents.

Suitable carriers, diluents, excipients, etc. can be found in standard pharmaceutical texts. See, for example, *Handbook of Pharmaceutical Additives,* 2nd Edition (eds. M. Ash and I. Ash), 2001 (Synapse Information Resources, Inc., Endicott, N.Y., USA), *Remington's Pharmaceutical Sciences,* 20th edition, pub. Lippincott, Williams & Wilkins, 2000; and *Handbook of Pharmaceutical Excipients,* 5th edition, 2005.

The term "pharmaceutically acceptable," as used herein, pertains to compounds, ingredients, materials, compositions, dosage forms, etc., which are, within the scope of sound medical judgment, suitable for use in contact with the tissues of the subject in question (e.g., human) without excessive toxicity, irritation, allergic response, or other problem or complication, commensurate with a reasonable benefit/risk ratio. Each carrier, diluent, excipient, etc. must also be "acceptable" in the sense of being compatible with the other ingredients of the formulation.

The formulations may be prepared by any methods well known in the art of pharmacy. Such methods include the step of bringing into association the compound with a carrier which constitutes one or more accessory ingredients. In general, the formulations are prepared by uniformly and intimately bringing into association the compound with carriers (e.g., liquid carriers, finely divided solid carrier, etc.), and then shaping the product, if necessary.

The formulation may be prepared to provide for rapid or slow release; immediate, delayed, timed, or sustained release; or a combination thereof.

Formulations suitable for oral administration (e.g., by ingestion) include liquids, solutions (e.g., aqueous, non-aqueous), suspensions (e.g., aqueous, non-aqueous), emulsions (e.g., oil-in-water, water-in-oil), elixirs, syrups, electuaries, tablets, granules, powders, capsules, cachets, pills, ampoules, boluses.

Tablets may be made by conventional means, e.g., compression or moulding, optionally with one or more accessory ingredients. Compressed tablets may be prepared by compressing in a suitable machine the compound in a free-flowing form such as a powder or granules, optionally mixed with one or more binders (e.g., povidone, gelatin, acacia, sorbitol, tragacanth, hydroxypropylmethyl cellulose); fillers or diluents (e.g., lactose, microcrystalline cellulose, calcium hydrogen phosphate); lubricants (e.g., magnesium stearate, talc, silica); disintegrants (e.g., sodium starch glycolate, cross-linked povidone, cross-linked sodium carboxymethyl cellulose); surface-active or dispersing or wetting agents (e.g., sodium lauryl sulfate); preservatives (e.g., methyl p-hydroxybenzoate, propyl p-hydroxybenzoate, sorbic acid); flavours, flavour enhancing agents, and sweeteners. Moulded tablets may be made by moulding in a suitable machine a mixture of the powdered compound moistened with an inert liquid diluent. The tablets may optionally be coated or scored and may be formulated so as to provide slow or controlled release of the compound therein using, for example, hydroxypropylmethyl cellulose in varying proportions to provide the desired release profile. Tablets may optionally be provided with a coating, for example, to affect release, for example an enteric coating, to provide release in parts of the gut other than the stomach.

Formulations suitable for parenteral administration (e.g., by injection), include aqueous or non-aqueous, isotonic, pyrogen-free, sterile liquids (e.g., solutions, suspensions), in which the compound is dissolved, suspended, or otherwise provided (e.g., in a liposome or other microparticulate). Such liquids may additional contain other pharmaceutically acceptable ingredients, such as anti-oxidants, buffers, preservatives, stabilisers, bacteriostats, suspending agents, thickening agents, and solutes which render the formulation isotonic with the blood (or other relevant bodily fluid) of the intended recipient. Examples of excipients include, for example, water, alcohols, polyols, glycerol, vegetable oils, and the like. Examples of suitable isotonic carriers for use in such formulations include Sodium Chloride Injection, Ringer's Solution, or Lactated Ringer's Injection. Typically, the concentration of the compound in the liquid is from about 1 ng/ml to about 10 µg/ml, for example from about 10 ng/ml to about 1 µg/ml. The formulations may be presented in unit-dose or multi-dose sealed containers, for example, ampoules and vials, and may be stored in a freeze-dried (lyophilised) condition requiring only the addition of the sterile liquid carrier, for example water for injections, immediately prior to use. Extemporaneous injection solutions and suspensions may be prepared from sterile powders, granules, and tablets.

Dosage

It will be appreciated by one of skill in the art that appropriate dosages of the compound of Formula (5) or Formula (6) and compositions comprising the compound can vary from patient to patient. Determining the optimal dosage will generally involve the balancing of the level of therapeutic benefit against any risk or deleterious side effects. The selected dosage level will depend on a variety of factors including the activity of the particular compound, the route of administration, the time of administration, the rate of excretion of the compound, the duration of the treatment, other drugs, compounds, and/or materials used in combination, the severity of the disorder, and the species, sex, age, weight, condition, general health, and prior medical history of the patient. The amount of compound and route of administration will ultimately be at the discretion of the physician, veterinarian, or clinician, although generally the dosage will be selected to achieve local concentrations at the site of action which achieve the desired effect without causing substantial harmful or deleterious side-effects.

Administration can be effected in one dose, continuously or intermittently (e.g., in divided doses at appropriate intervals) throughout the course of treatment. Methods of determining the most effective means and dosage of administration are well-known to those of skill in the art and will vary with the formulation used for therapy, the purpose of the therapy, the target cell(s) being treated, and the subject being treated. Single or multiple administrations can be carried out with the dose level and pattern being selected by the treating physician, veterinarian, or clinician.

Examples of Some Preferred Formulations

A preferred formulation is a dosage unit (e.g., a pharmaceutical tablet or capsule) comprising 20 to 300 mg of a compound of Formula (5) or Formula (6) as described herein; and a pharmaceutically acceptable carrier, diluent, or excipient.

In some embodiments, the dosage unit is a tablet.

In some embodiments, the dosage unit is a capsule.

In some embodiments, said capsules are gelatine capsules.

In some embodiments, said capsules are HPMC (hydroxypropylmethylcellulose) capsules.
In some embodiments, the amount is 30 to 200 mg.
In some embodiments, the amount is about 30 mg.
In some embodiments, the amount is about 60 mg.
In some embodiments, the amount is about 100 mg.
In some embodiments, the amount is about 150 mg.
In some embodiments, the amount is about 200 mg.

The dosage amounts as set out above may refer to the amount of the compound itself or may refer to the amount of free base equivalent contained in the dosage unit. Both of these alternatives are specifically and explicitly disclosed by the present disclosure.

In some embodiments, the pharmaceutically acceptable carrier, diluent, or excipient is or comprises one or both of a glyceride (e.g., Gelucire 44/14®; lauroyl macrogol-32 glycerides PhEur, USP) and colloidal silicon dioxide (e.g., 2% Aerosil 200®; Colliodal Silicon Dioxide PhEur, USP).

EXAMPLES

The following examples are provided solely to illustrate the present invention and are not intended to limit the scope of the invention, as described herein.

Method 1

Thiosulphonic acid S-(2-amino-5-dimethyl amino) phenyl ester

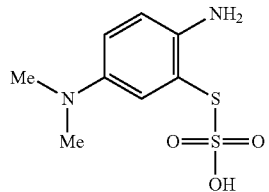 [SMILES: CN(C)c1ccc(N)c(SS(=O)(=O)O)c1]

N,N-Dimethyl-p-phenylenediamine (10 g, 136.2 g/mol, 73.4 mmol, 1.0 equivalent) and water (200 mL) was added to a multi-necked round bottom flask.

The reaction mixture was cooled and maintained at 5° C. using an ice/water cooling bath and stirred for 10 minutes.

Aluminium sulphate hexadecahydrate ($Al_2(SO_4)_3 \cdot 16H_2O$) (23.14 g, 630.39 g/mol, 36.7 mmol, 0.5 equivalents) was added to the reaction mixture in one portion.

After 5 minutes, a solution of sodium thiosulphate ($Na_2S_2O_3 \cdot 5H_2O$, 20.04 g, 248.18 g/mol, 80.7 mmol, 1.1 equivalents, dissolved in 20 mL of water) was added to the reaction mixture as a single portion.

After another 5 minutes, potassium persulphate ($K_2S_2O_8$, 19.86 g, 270.32 g/mol, 73.5 mmol, 1.0 equivalents) was added to the reaction mixture over a 10 minute period. A rise in temperature from 5° C. to 11° C. was observed.

The reaction mixture was stirred for another 2 hours, whilst maintained at 5° C. using an ice/water cooling bath.

The reaction mixture was warmed over a 30 minute period to 20° C.

The solid product was collected by filtration and washed with 50° C. water (3×20 mL).

The filter cake was then washed with ethyl acetate (20 mL) and dried on the filter under suction for 20 minutes.

The solid was further dried in a vacuum oven (50° C. at <950 mbar) to achieve a constant weight and provide the crude product as a black/purple solid with white flakes (15.791 g).

The product was characterised using NMR: $^1$H NMR (300 MHz, $D_2O$): δ=7.22 (s, 1H, Ar—H), 7.07 (m, 2H, Ar—H), 3.01 (d, 6H, $CH_3$).

FIG. 1 shows the $^1$H NMR (300 MHz, DMSO-$d_6$) spectrum for thiosulphonic acid S-(2-amino-5-dimethyl amino) phenyl ester obtained in Method 1.

A DMSO-$d_6$ solution of equimolar amounts of the crude product and a reference standard (3-(trimethylsilyl)-1-propanesulfonic acid (97%)) was analysed by proton nuclear magnetic resonance spectroscopy ($^1$H NMR).

Figure 2:
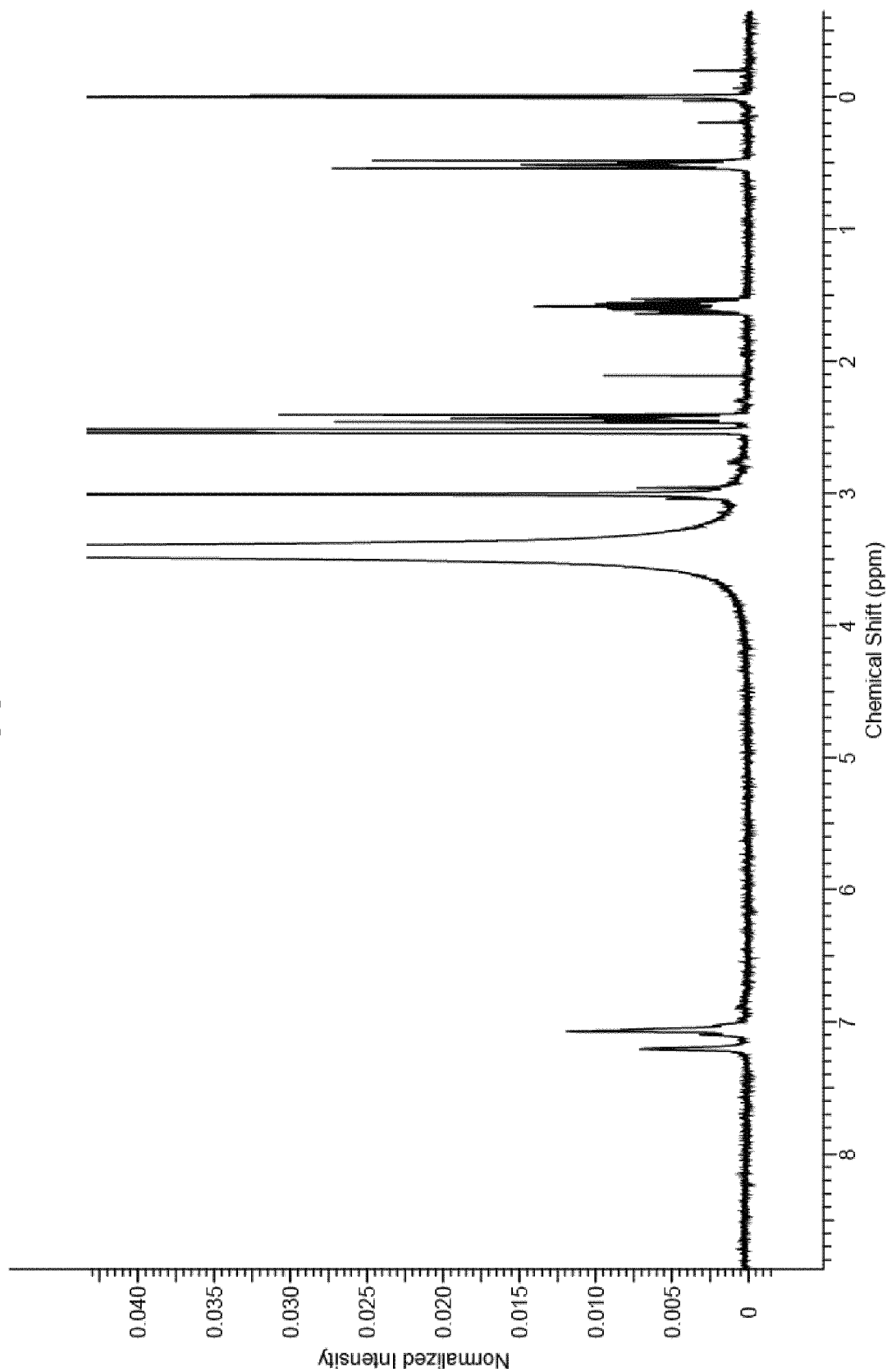
FIG. 2 shows the $^1$H NMR (300 MHz, DMSO-$d_6$) spectrum for a mixture of thiosulphonic acid S-(2-amino-5-dimethyl amino) phenyl ester obtained in Method 1 and the reference compound 3-(trimethylsilyl)-1-propanesulfonic acid.

FIG. 2 shows the $^1$H NMR (300 MHz, DMSO-$d_6$) spectrum for a mixture of thiosulphonic acid S-(2-amino-5-dimethyl amino) phenyl ester obtained in Method 1 and the reference compound 3-(trimethylsilyl)-1-propanesulfonic acid.

From the $^1$H NMR spectrum (FIG. 2), a purity of 87% was calculated. A residual inorganic salt can be seen as the white flakes within the sample. The amount of target compound (thiosulphonic acid S-(2-amino-5-dimethyl amino) phenyl ester) in the crude material was calculated to be 13.74 g (75% yield). The crude material was used in the subsequent reaction step without further purification.

Method 2A (4-(2-(Thiosulfate)-4-(dimethylamino)-phenyl-imino)-cyclohex-2,5-dienylidene)-N,N-dimethyl ammonium

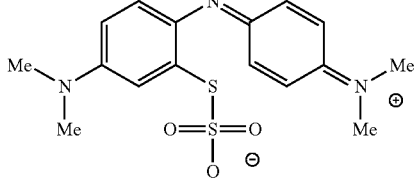

N,N-dimethylaniline ($C_6H_6N(CH_3)_2$, 2.89 g, 121.18 g/mol, 23.8 mmol, 1.0 equivalent) and water (79 mL) were added to a multi-necked round bottom flask.

Sulphuric acid ($H_2SO_4$, 98%, 1.17 g, 98.08 g/mol, 11.9 mmol, 0.5 equivalents) was added to the reaction mixture drop-wise over 10 minutes.

Crude thiosulphonic acid S-(2-amino-5-dimethyl amino) phenyl ester (7.89 g which contains 5.92 g, 248.32 g/mol, 23.8 mmol, 1.0 equivalent) was added to the reaction mixture in a single aliquot to form a suspension.

The reaction mixture was cooled to 5° C. and maintained at 5° C. using an ice/water cooling bath and stirred for over 10 minutes.

Sodium periodate ($NaIO_4$, 10.66 g, 213.89 g/mol, 49.8 mmol, 2.09 equivalents) was added to the reaction mixture in aliquots of about 1 g over a 40 minute period while maintained at 5° C. to form a green slurry.

The reaction mixture was stirred for 2 hours while maintained at 5° C.

The reaction mixture was filtered and the solid filter cake washed with pre-heated (50° C.) water (2×20 mL) and dried on the filter under suction for 20 minutes.

A wet mass of 23 g of crude product was obtained, and was used in the subsequent reaction step without further drying or purification.

Method 2B (4-(2-(Thiosulfate)-4-(dimethylamino)-phenyl-imino)-cyclohex-2,5-dienylidene)-N,N-dimethyl ammonium

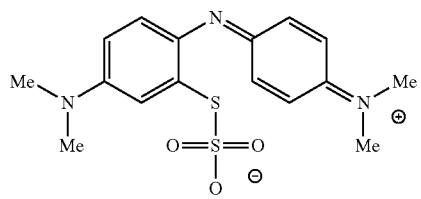

N,N-dimethylaniline ($C_6H_5N(CH_3)_2$, 4.88 g, 121.18 g/mol, 40.3 mmol, 1.0 equivalent) and water (100 mL) were added to a multi-necked round bottom flask.

Sulphuric acid ($H_2SO_4$, 98%, 1.97 g, 98.08 g/mol, 20.1 mmol, 0.5 equivalents) was added to the reaction mixture drop-wise over 10 minutes.

Thiosulphonic acid S-(2-amino-5-dimethyl amino) phenyl ester (10.0 g, 248.32 g/mol, 40.3 mmol, 1.0 equivalent) was added to the reaction mixture in a single aliquot to form a suspension.

The reaction mixture was cooled to 5° C. and maintained at 5° C. using an ice/water cooling bath and stirred for 10 minutes.

Sodium periodate ($NaIO_4$, 17.67 g, 213.89 g/mol, 82.6 mmol, 2.05 equivalents) was added in aliquots of about 1 g over a 90 minute period while maintained at 5° C. to form a green slurry.

The reaction mixture was stirred for 2 hours while maintained at 5° C.

The reaction mixture was filtered and the solid filter cake washed with water (2×40 mL) and dried on the filter under suction for 20 minutes.

The filter cake was re-slurried with fresh water (100 mL) and stirred for 20 minutes.

The slurry was then re-filtered and the solid filter cake washed with water (40 mL) and dried on the filter under suction for 30 minutes.

The solid was further dried under vacuum (<900 mbar) at 20° C. for 48 hours to provide a green powder (12.78 g).

The product was characterized, and the resulting data are summarized in the following table.

TABLE 1

| Characterisation of Product of Method 2B | |
|---|---|
| Weight loss on drying (Karl Fischer) | 7.32% |
| $^1$H NMR (300 MHz, DMSO-$d_6$) | δ = 3.34 (s, 6H), 3.45 (s, 6H), 7.13-7.37 (m, 6H), 7.95 (s, 1H) |
| $v_{max}$ (cm$^{-1}$) | 1594(m), 1411(m), 1360 (m), 1331 (m), 1161 (s), 1015 (s), 869 (m), 627 (s) |
| MS, m/z (ES+) | Theoretical: [M + Na]$^+$ 389.0844 (amu) |
| Accurate Mass | Measured: [M + Na]$^+$ 389.0837 (amu) |
| HPLC (a/a) | 74.74% |
| Accurate yield | 59% |

Figure 3:
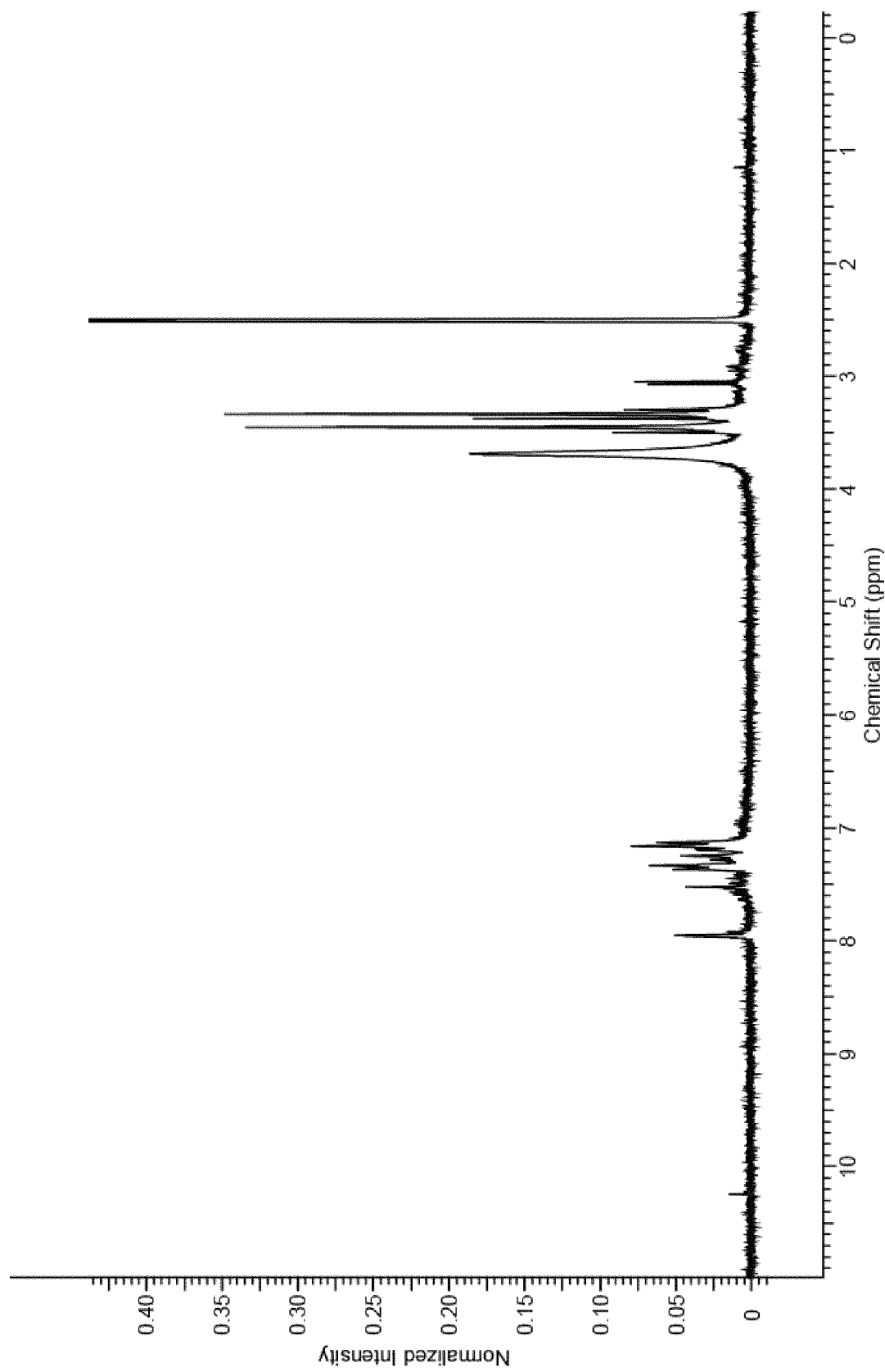
FIG. 3 shows the $^1$H NMR (300 MHz, DMSO-$d_6$) spectrum for (4-(2-(thiosulfate)-4-(dimethylamino)-phenyl-imino)-cyclohex-2,5-dienylidene)-N,N-dimethyl ammonium obtained in Method 2B.

FIG. 3 shows the $^1$H NMR (300 MHz, DMSO-$d_6$) spectrum for (4-(2-(thiosulfate)-4-(dimethylamino)-phenyl-imino)-cyclohex-2,5-dienylidene)-N,N-dimethyl ammonium obtained in Method 2B.

Method 3

Methylthioninium Chloride (MTC)

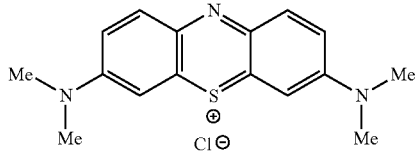 [SMILES: CN(C)c1ccc2nc3ccc(N(C)C)cc3[s+]c2c1 ; [Cl-]]

Crude (4-(2-(thiosulfate)-4-(dimethylamino)-phenyl-imino)-cyclohex-2,5-dienylidene)-N,N-dimethyl ammonium (prepared by Method 2A, approximately 23 g of crude product), water (100 mL) and copper (II) sulphate ($CuSO_4 \cdot 5H_2O$, 0.98 g, 249.68 g/mol, 3.93 mmol, 0.165 equivalents based on the thiosulphonic acid used in Method 2A) were added to a multi-necked round bottom flask form a slurry.

The reaction mixture was heated at 85° C. and stirred for 1 hour during which time an intense blue colour developed.

The reaction mixture was then filtered while at 85° C., and the solid waste in the filter was washed with pre-heated (50° C.) water (2×10 mL).

The combined filtrate from the reaction liquor and washings was then cooled to 35° C. over 30 minutes, during which air was bubbled through the blue solution.

Hydrochloric acid (HCl, 32%, 12 mL) was added and the reaction mixture was stirred for 14 hours to allow crystallisation.

The product was collected by filtration and washed with pre-chilled (5° C.) water (2×10 mL), which had been acidified with hydrochloric acid to pH 1.

The product was then washed with toluene (10 mL), dried on the filter under suction for 20 minutes, and then dried in a fan-assisted oven at 40° C. for 9 hours to provide (green crystalline needles) (3.93 g).

The product was characterized, and the resulting data are summarized in the following table.

TABLE 2

| Characterisation of Product of Method 3 | |
|---|---|
| Weight loss on drying (moisture balance) | 11.00% |
| $^1$H NMR (300 MHz, $D_2O$) | δ = 3.03 (d, 12H), 6.73 (d, J = 2.6 Hz, 2H), 6.95 (dd, J = 9.6 Hz, 2H), 7.22 (d, J = 9.7 Hz, 2H) |
| $^{13}$C NMR (75 MHz, $D_2O$) | δ = 40.49 (4C), 106.00 (2C), 118.32 (2C), 133.75 (2C), 134.00 (2C), 136.27 (2C), 1523.15 (2C) |
| $v_{max}$ (cm$^{-1}$) | 3351 (b, $H_2O$ 'Solvate'), 1592(s), 1486(m), 1391(s), 1334(s), 1176(m), 1137(m), 878(s) |
| MS, m/z (ESI) | [M$^+$] 284 |
| HPLC (w/w) | 82.63% |
| Accurate yield of MTC (*) | 42% |

(*) The yield of MTC is reported with respect to the starting material, N,N-dimethylaniline, used in Method 2A. That is, the yield reported is the yield over two steps, Method 2A and Method 3. The yield of MTC over three steps, Method 1, Method 2A and Method 3, with respect to the N,N-Dimethyl-p-phenylenediamine starting material from Method 1 is 28%.

Figure 4:
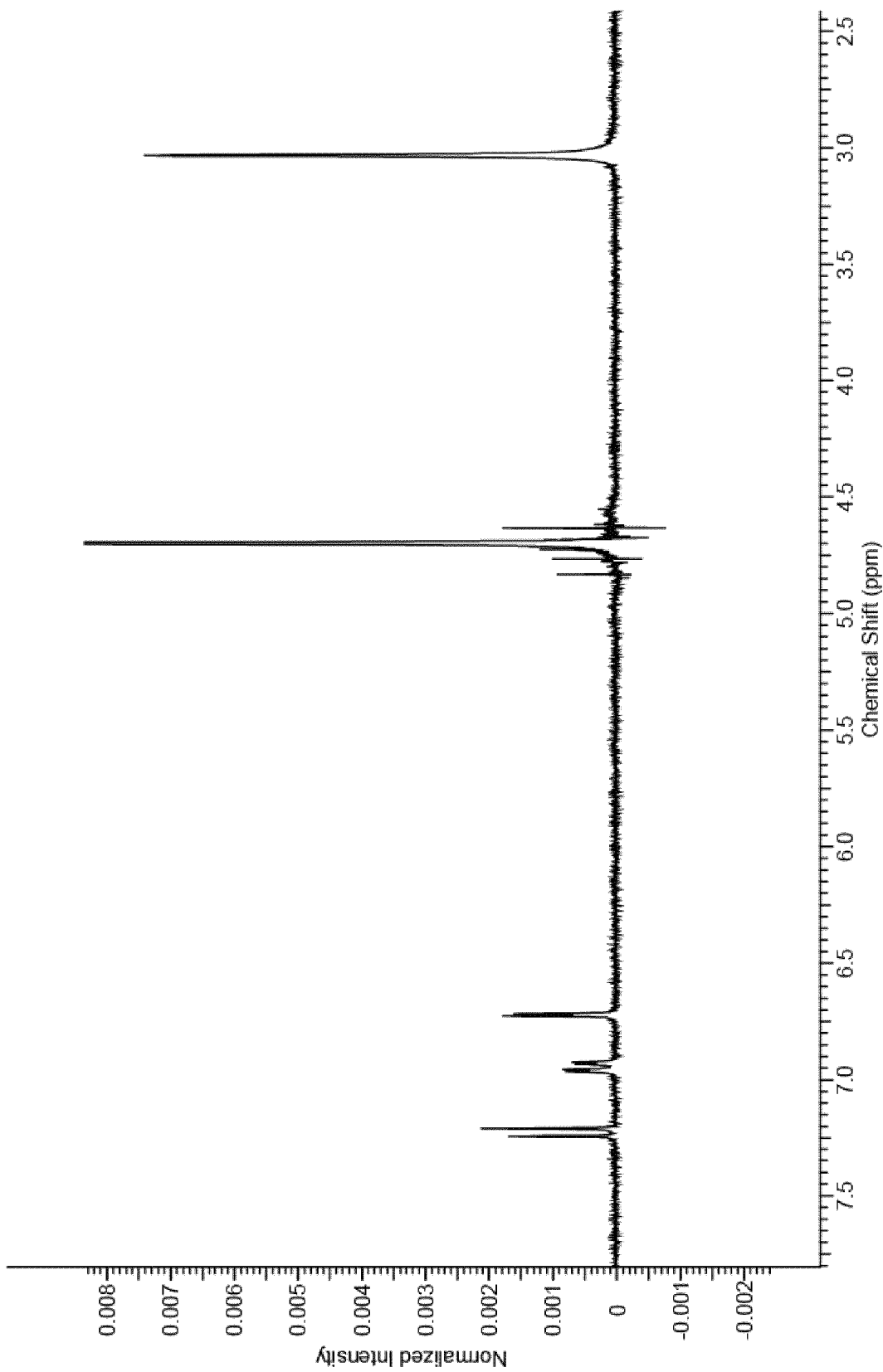
FIG. 4 shows the $^1$H NMR (300 MHz, D$_2$O) spectrum for methylthioninium chloride (MTC) obtained in Method 3.

FIG. 4 shows the $^1$H NMR (300 MHz, $D_2O$) spectrum for methylthioninium chloride (MTC) obtained in Method 3.

The organic purity of the methylthioninium chloride (MTC) product was determined by HPLC analysis and the results are summarised in the following table.

TABLE 3

HPLC Purity of MTC Product

| Compound | % (a/a) | % (w/w) |
|---|---|---|
| MTC | 97.11 | 82.63 |
| Azure B | 2.60 | 2.20 |
| Azure A | 0.17 | <0.05(*) |
| Azure C |  |  |
| MVB | <0.05 (*) | 0.14 |
| MVB-CH$_3$ |  |  |
| sDMT | <0.05 (*) | <0.05 (*) |
| Others | 0.12 | ND |
| Total | 100 | 84.97 |

(*) The "<0.05" amounts are ignored in the calculation of the "total".

The term "others" refers to all other compounds that are present, for which a specific value is not reported.

As used herein, "HPLC % (a/a)" refers to "HPLC percent area by area", and denotes the ratio of the area under the HPLC peak associated with the chemical species to the total area under all of the HPLC peaks observed, expressed as a percent. For example, "Azure B % (a/a)" denotes the ratio of the area under the HPLC peak associated with Azure B to the total area under all of the HPLC peaks observed, multiplied by 100.

Similarly, as used herein, "HPLC % (w/w)" refers to "HPLC percent weight by weight", and denotes the ratio of the area under the HPLC peak compared with the area under the HPLC peak of a reference standard, expressed as a percent. For example, "Azure B % (w/w)" denotes the ratio of the area under the Azure B peak compared against the area under the peak of an Azure B reference standard of known concentration, multiplied by 100.

TABLE 4

System Parameters for HPLC Purity Analysis of MTC

| | |
|---|---|
| HPLC system | Agilent 1200 with DAD and data handling capacity |
| Column | Agilent Eclipse XDB-Phenyl, 150 × 4.6 mm, 3.5 µm particle size |
| Column Temperature | 50° C. |
| Autosampler Temperature | 5° C. |
| Mobile Phase | A: 0.1% v/v trifluoroacetic acid B: Acetonitrile |
| Flow Rate | 1.5 mL/min |
| Injection volume | 50 µL |
| Stop time | 25.0 min |
| Wavelength | 284 nm, slit width 4 nm |

TABLE 5

Solvent Gradient Parameters for HPLC Purity Analysis of MTC

| Time, min | A, % | B, % | Flow, mL/min |
|---|---|---|---|
| 0 | 90 | 10 | 1.5 |
| 1 | 90 | 10 | 1.5 |
| 13 | 75 | 25 | 1.5 |
| 18 | 40 | 60 | 1.5 |
| 20 | 40 | 60 | 1.5 |
| 20.1 | 90 | 10 | 1.5 |
| 25 | 90 | 10 | 1.5 |

HPLC standards and samples were prepared as follows: Fresh MTC reference material always used when preparing MTC stock and lower limit of quantification (LLOQ) standards. Stock and LLOQ standards were used for determination of retention time and quantification. 25 and 100 mL amber-glass volumetric flasks used to prepare standards and samples.

Concentrated solutions were prepared using 34-38 mg of sample. The sample was dissolved in 50 mL of diluent (90:10, 0.1% TFA: acetonitrile), sonicated for 5 minutes, and then diluted to the graduation mark with diluent. Solutions were then allowed to stand for 1 hour prior to a 1:10 dilution.

For runs, 2 L of 0.1% TFA and 1 L of acetonitrile was used for the eluents.

TABLE 6

Typical Retention Times for HPLC Purity Analysis of MTC (at 284 nm)

| Compound | Retention time (minutes) |
|---|---|
| Thionine | 8.66 |
| MVB-CH$_3$ | 10.19 |
| Azure C | 10.92 |
| MVB | 11.72 |
| Azure A | 13.22 |
| sDMT | 13.50 |
| Azure B | 15.59 |
| MTC | 16.58 |

For reference, the chemical structures of MTC and the related impurities are shown in the following table.

TABLE 7

Chemical Structures of MTC and Related Impurities

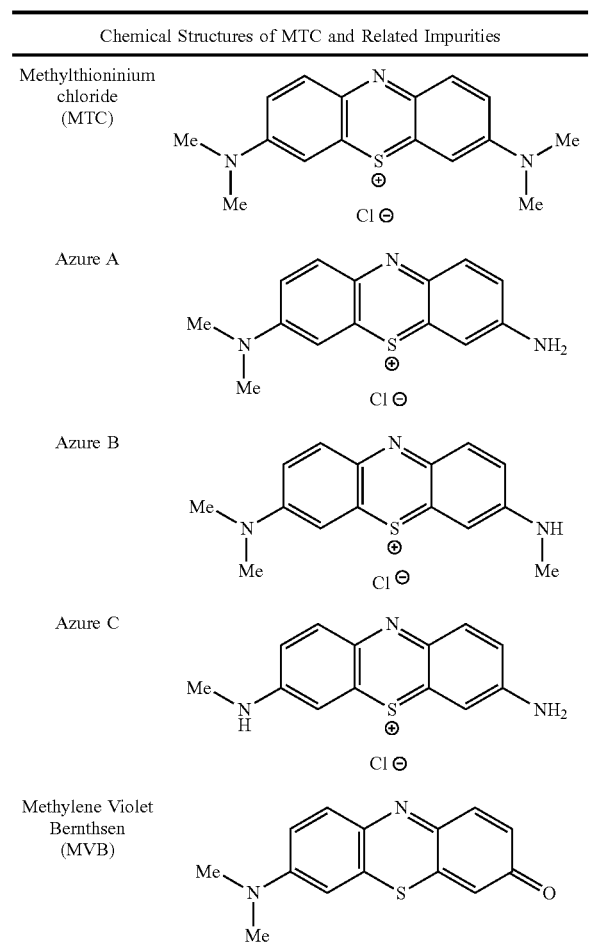

TABLE 7-continued

Chemical Structures of MTC and Related Impurities

| | |
|---|---|
| 7-(methylamino)-3H-phenothiazine-3-one (MVB-CH₃) | |
| 7-amino-3H-phenothiazine-3-one (MVB-2CH₃) | |
| Thionine | |
| Symmetrical Dimethyl Thionine (sDMT) | |

The foregoing has described the principles, preferred embodiments, and modes of operation of the present invention. However, the invention should not be construed as limited to the particular embodiments discussed. Instead, the above-described embodiments should be regarded as illustrative rather than restrictive. It should be appreciated that variations may be made in those embodiments by workers skilled in the art without departing from the scope of the present invention.

REFERENCES

A number of publications are cited herein in order to more fully describe and disclose the invention and the state of the art to which the invention pertains. Full citations for these references are provided below. Each of these references is incorporated herein by reference in its entirety into the present disclosure, to the same extent as if each individual reference was specifically and individually indicated to be incorporated by reference.

Badische Anilin- und Soda-Fabrik, 1877, "Verfahren Zur Darstellung Blauer Farbstoffe Aus Dimethyl-Anilin Und Anderen Tertiaren Aromatischen Monaminen," German Patent No. 1886, published 15 Dec. 1877.

Bernthsen, August, 1885a, "Studien in der Methylenblaugruppe," Justus Liebig's Annalen der Chemie, Band 230, pp. 73-136.

Bernthsen, August, 1885b, "Studien in der Methylenblaugruppe," Justus Liebig's Annalen der Chemie, Band 230, pp. 137-211.

Bernthsen, August, 1889, "Studien in der Methylenblaugruppe," Justus Liebig's Annalen der Chemie, Band 251, pp. 1-96.

Burkett et al., "In vivo stain composition, process of manufacture, and methods of use to identify dysplastic tissue", European Patent Publication No 0 966 957 A2, published 29 Dec. 1999.

Colour Index, Vol. 4 (3rd Edition, 1971), p. 4470, Entry Number 52015.

Fierz-David and Blangley, 1949, "F. Oxazine and Thiazine Dyes," in: *Fundamental Processes of Dye Chemistry*, published by Interscience (London, UK), pp. 308-314.

Guttmann and Ehrlich, 1891, "Uber die wirkung des methylenblau bei malaria," Berl. Klin. Woschenr., Vol. 28, pp. 953-956.

Larch et al., 2010, "Methods of chemical synthesis diaminophenothiazinium compounds involving the use of persulfate oxidants", International (PCT) patent publication number WO 2010/130977 A1 published 18 Nov. 2010.

Leventis, N., et al., 1997, "Synthesis of Substituted Phenothiazines Analogous to Methylene Blue by Electrophilic and Nucleophilic Aromatic Substitutions in Tandem. A Mechanistic Perspective," Tetrahedron, Vol. 53, No. 29, pp. 10083-10092.

Lillie, R. D., et al., 1979, "Zinc Chloride Methylene Blue, I. Biological Stain History, Physical Characteristics and Approximation of Azure B Content of Commercial Samples," *Stain Technology*, Vol. 54, No. 1, pp. 33-39.

Masuya, Hirotomo, 1992, "Phenothiazine Derivatives, Their Production and Use," European Patent Publication No 0 510 668 A2, published 28 Oct. 1992.

Randvere et al., 1980, "Process for preparing methylene blue", United States of America (US) patent publication number U.S. Pat. No. 4,212,971 A, published 15 Jul. 1980.

Rengelshausen et al., 2004, "Pharmacokinetic interaction of chloroquine and methylene blue combination against malaria," European Journal of Clinical Pharmacology, Vol. 60, pp. 709-715.

Rongxian et al., 2015, "Preparation method of methylene blue", Chinese (CN) patent publication number CN105130926, published 9 Dec. 2015.

Schirmer et al., 2003, "Methylene blue as an antimalarial agent," Redox Report, Vol. 8, pp. 272-275.

Sinclair et al., 2015, "Methods of chemical synthesis of diaminophenothiazinium compounds including methylthioninium chloride (MTC)", international (PCT) patent publication number WO 2015/052496 A1 published 16 Apr. 2015.

Storey et al., 2006, "Methods of chemical synthesis and purification of diaminophenothiazinium compounds including methylthioninium chloride (MTC)", international (PCT) publication number WO 2006/032879 A2, published 20 Mar. 2006.

Wischik et al., 1988a, PNAS USA, Vol. 85, pp. 4506-4510.

Wischik et al., 1988b, PNAS USA, Vol. 85, pp. 4884-4888.

Wischik et al., 1996a, PNAS USA, Vol. 93, pp. 11213-11218.

Wischik et al., 1996b, "Inhibition of Tau-Tau-Association", international (PCT) patent publication number WO 96/30766 A1, published 3 Oct. 1996.

Wischik et al., 1997, in "Brain microtubule-associated proteins: modifications in disease", Eds. Avila, J., Brandt, R. and Kosik, K. S. (Harwood Academic Publishers, Amsterdam) pp. 185-241.

Wischik et al., 2001, in "Neurobiology of Alzheimer's Disease", 2nd Edition, 2001, Eds. Dawbarn, D. and Allen, S. J., The Molecular and Cellular Neurobiology Series, Bios Scientific Publishers, Oxford).

Wischik et al., 2002, "Materials and Methods Relating to Protein Aggregation in Neurodegenerative Disease", international (PCT) patent publication number WO 02/055720 A2, published 18 Jul. 2002.

Wischik et al., 2007, "3,6-Diamino-10H-phenothiazine Salts and Their Use", international (PCT) patent publication number WO 2007/110627 A2 published 4 Oct. 2007.

Wischik et al., 2007, "Thioninium Compounds and Their Use", international (PCT) patent publication number WO 2007/110630 A1, published 4 Oct. 2007.

Zhou et al., 2006, "Medicinal methylene blue synthesis method", Chinese (CN) patent publication number CN1970548, published 30 May 2007.

The invention claimed is:

1. A method of chemical synthesis of a compound of Formula (1):

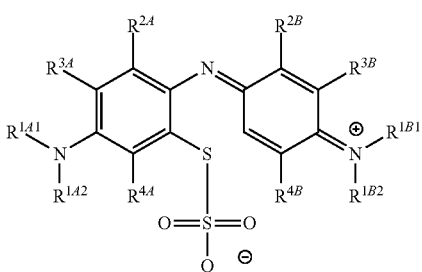

comprising a step of periodate mediated oxidative coupling, in which a compound of Formula (2):

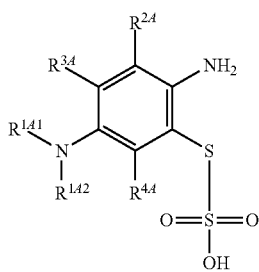

is reacted with a compound of Formula (3):

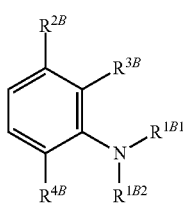

and a periodate oxidising agent;
to form said compound of Formula (1);
wherein:
—$R^{1A1}$ is independently $C_{1-4}$alkyl; $C_{2-4}$alkenyl; halogenated $C_{1-4}$alkyl; $C_{5-10}$aryl; halogenated $C_{5-10}$aryl; $C_{5-10}$aryl-$C_{1-4}$alkyl; or halogenated $C_{5-10}$aryl-$C_{1-4}$alkyl;
—$R^{1A2}$ is independently $C_{1-4}$alkyl; $C_{2-4}$alkenyl; halogenated $C_{1-4}$alkyl; $C_{5-10}$aryl; halogenated $C_{5-10}$aryl; $C_{5-10}$aryl-$C_{1-4}$alkyl; or halogenated $C_{5-10}$aryl-$C_{1-4}$alkyl;
—$R^{1B1}$ is independently $C_{1-4}$alkyl; $C_{2-4}$alkenyl; halogenated $C_{1-4}$alkyl; $C_{5-10}$aryl; halogenated $C_{5-10}$aryl; $C_{5-10}$aryl-$C_{1-4}$alkyl; or halogenated $C_{5-10}$aryl-$C_{1-4}$alkyl;
—$R^{1B2}$ is independently $C_{1-4}$alkyl; $C_{2-4}$alkenyl; halogenated $C_{1-4}$alkyl; $C_{5-10}$aryl; halogenated $C_{5-10}$aryl; $C_{5-10}$aryl-$C_{1-4}$alkyl; or halogenated $C_{5-10}$aryl-$C_{1-4}$alkyl;
—$R^{2A}$ is independently —H or —$R^{3AA}$;
—$R^{2AA}$ is independently $C_{1-4}$alkyl; $C_{2-4}$alkenyl; halogenated $C_{1-4}$alkyl; $C_{5-10}$aryl; halogenated $C_{5-10}$aryl; $C_{5-10}$aryl-$C_{1-4}$alkyl; or halogenated $C_{5-10}$aryl-$C_{1-4}$alkyl;
—$R^{2B}$ is independently —H or —$R^{3AA}$;
—$R^{2BB}$ is independently $C_{1-4}$alkyl; $C_{2-4}$alkenyl; halogenated $C_{1-4}$alkyl; $C_{5-10}$aryl; halogenated $C_{5-10}$aryl; $C_{5-10}$aryl-$C_{1-4}$alkyl; or halogenated $C_{5-10}$aryl-$C_{1-4}$alkyl;
—$R^{3A}$ is independently —H or —$R^{3AA}$;
—$R^{3AA}$ is independently $C_{1-4}$alkyl; $C_{2-4}$alkenyl; halogenated $C_{1-4}$alkyl; $C_{5-10}$aryl; halogenated $C_{5-10}$aryl; $C_{5-10}$aryl-$C_{1-4}$alkyl; or halogenated $C_{5-10}$aryl-$C_{1-4}$alkyl;
—$R^{3B}$ is independently —H or —$R^{3BB}$;
—$R^{3BB}$ is independently $C_{1-4}$alkyl; $C_{2-4}$alkenyl; halogenated $C_{1-4}$alkyl; $C_{5-10}$aryl; halogenated $C_{5-10}$aryl; $C_{5-10}$aryl-$C_{1-4}$alkyl; or halogenated $C_{5-10}$aryl-$C_{1-4}$alkyl;
—$R^{4A}$ is independently —H or —$R^{4AA}$;
—$R^{4AA}$ is independently $C_{1-4}$alkyl; $C_{2-4}$alkenyl; halogenated $C_{1-4}$alkyl; $C_{5-10}$aryl; halogenated $C_{5-10}$aryl; $C_{5-10}$aryl-$C_{1-4}$alkyl; or halogenated $C_{5-10}$aryl-$C_{1-4}$alkyl;
—$R^{4B}$ is independently —H or —$R^{4BB}$; and
—$R^{4BB}$ is independently $C_{1-4}$alkyl; $C_{2-4}$alkenyl; halogenated $C_{1-4}$alkyl; $C_{5-10}$aryl; halogenated $C_{5-10}$aryl; $C_{5-10}$aryl-$C_{1-4}$alkyl; or halogenated $C_{5-10}$aryl-$C_{1-4}$alkyl.

2. A method according to claim 1, wherein each —$R^{1A1}$ is independently $C_{1-4}$alkenyl; $C_{2-4}$alkenyl; or halogenated $C_{1-4}$alkyl.

3. A method according to claim 1, wherein —$R^{1A2}$ is independently $C_{1-4}$alkyl; $C_{2-4}$alkenyl; or halogenated $C_{1-4}$alkyl preferably.

4. A method according to claim 1, wherein —$R^{1B1}$ is independently $C_{1-4}$alkenyl; $C_{2-4}$alkentl; or halogenated $C_{1-4}$alkyl.

5. A method according to claim 1, wherein —$R^{1B2}$ is independently $C_{1-4}$alkyl; $C_{2-4}$alkenyl; or halogenated $C_{1-4}$alkyl.

6. A method according to claim 1, wherein —$R^{2AA}$, if present, is independently $C_{1-4}$alkyl; $C_{2-4}$alkenyl; or halogenated $C_{1-4}$alkyl.

7. A method according to claim 1, wherein —$R^{2BB}$, if present, is independently $C_{1-4}$alkyl; $C_{2-4}$alkenyl; or halogenated $C_{1-4}$alkyl.

8. A method according to claim 1, wherein —$R^{3AA}$, if present, is independently $C_{1-4}$alkyl; $C_{2-4}$alkenyl; or halogenated $C_{1-4}$alkyl.

9. A method according to claim 1, wherein —$R^{3BB}$, if present, is independently $C_{1-4}$alkyl; $C_{2-4}$alkenyl; or halogenated $C_{1-4}$alkyl.

10. A method according to claim 1, wherein —$R^{4AA}$, if present, is independently $C_{1-4}$alkyl; $C_{2-4}$alkenyl; or halogenated $C_{1-4}$alkyl.

11. A method according to claim 1, wherein —$R^{4BB}$, if present, is independently $C_{1-4}$alkyl; $C_{2-4}$alkenyl; or halogenated $C_{1-4}$alkyl.

12. A method according to claim 1, wherein the periodate oxidizing agent is iodine peroxide, periodic acid or a periodate salt.

13. A method according to claim 12, wherein the periodate oxidizing agent is an alkali metal periodate salt such as a sodium periodate salt.

14. A method according to claim 1, wherein the ratio, A, of the amount of compound of Formula (2), in equivalents, to the amount of compound of Formula (3), in equivalents, is from about 0.5 to about 3.0.

15. A method according to claims 1, wherein the ratio, B, of the amount of compound of Formula (2), in equivalents, to the amount of compound of periodate oxidizing agent, in equivalents, is from about 0.5 to about 3.0.

16. A method according to claim 1, wherein the reaction is carried out in the presence of an acid.

17. A method according to claim 16, wherein the ratio, C, of the amount of compound of Formula (2), in equivalents, to the amount of H+ provided by the acid, in equivalents, is from about 0.5 to about 3.0.

18. A method according to claim 1, wherein the reaction is carried out in the presence of water.

19. A method according to claim 1, wherein the method further comprises a preceding step of:

converting a compound of Formula (4):

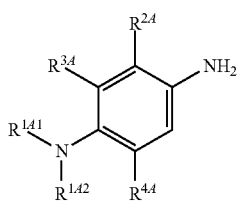

to the corresponding compound of Formula (2):

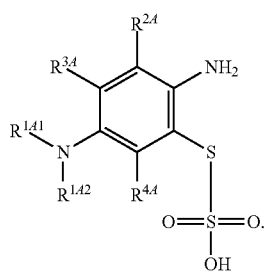

20. A method according to claim 1, wherein the method further comprises a subsequent step of:

converting the compound of Formula (1):

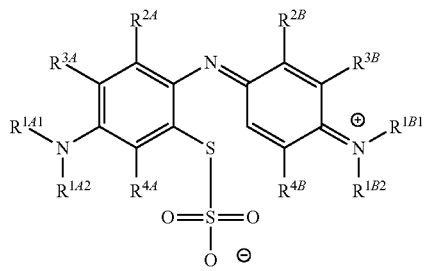

to the corresponding compound of Formula (5):

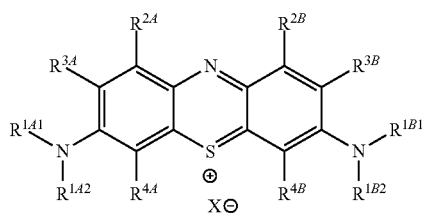

wherein $X^-$ is one or more anionic counter ions to achieve electrical neutrality.

21. A method according to claim 20, wherein the method further comprises a subsequent step of:

converting the compound of Formula (5):

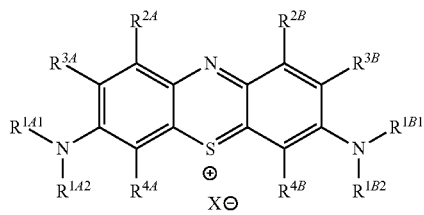

to the corresponding compound of Formula (6):

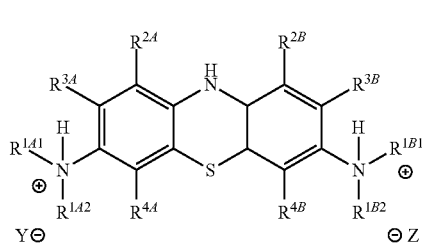

wherein $Y^-$ and $Z^-$, taken together, are one or more anionic counter ions to achieve electrical neutrality.

* * * * *